(12) United States Patent
Cheng et al.

(10) Patent No.: US 11,891,601 B2
(45) Date of Patent: Feb. 6, 2024

(54) METHOD TO ENHANCE THE TRANSCRIPTION REGULATION OF SUPT4H ON GENES CONTAINING REPETITIVE NUCLEOTIDE SEQUENCES

(71) Applicant: National Yang-Ming University, Taipei (TW)

(72) Inventors: Tzu-Hao Cheng, Taipei (TW); Chia-Rung Liu, Taipei (TW); Tse-I Lin, Taipei (TW); Yun-Yun Wu, Taipei (TW); Stanley N. Cohen, Stanford, CA (US)

(73) Assignee: NATIONAL YANG MING CHIAO TUNG UNIVERSITY, Taipei (TW)

( * ) Notice: Subject to any disclaimer, the term of this patent is extended or adjusted under 35 U.S.C. 154(b) by 99 days.

(21) Appl. No.: 16/963,772

(22) PCT Filed: Jan. 22, 2019

(86) PCT No.: PCT/CN2019/072597
§ 371 (c)(1),
(2) Date: Jul. 21, 2020

(87) PCT Pub. No.: WO2019/141279
PCT Pub. Date: Jul. 25, 2019

(65) Prior Publication Data
US 2021/0040479 A1    Feb. 11, 2021

Related U.S. Application Data

(60) Provisional application No. 62/620,308, filed on Jan. 22, 2018.

(51) Int. Cl.
| | |
|---|---|
| C12N 15/113 | (2010.01) |
| A61P 25/00 | (2006.01) |
| A61K 31/122 | (2006.01) |
| A61K 31/4745 | (2006.01) |
| A61K 31/7105 | (2006.01) |

(52) U.S. Cl.
CPC .......... *C12N 15/113* (2013.01); *A61K 31/122* (2013.01); *A61K 31/4745* (2013.01); *A61K 31/7105* (2013.01); *A61P 25/00* (2018.01); *C12N 2310/14* (2013.01); *C12N 2320/31* (2013.01)

(58) Field of Classification Search
None
See application file for complete search history.

(56) References Cited

U.S. PATENT DOCUMENTS

| | | | |
|---|---|---|---|
| 2004/0152651 A1* | 8/2004 | Rana | C12Y 207/11022 514/44 A |
| 2018/0064744 A1* | 3/2018 | Cohen | A61K 31/7064 |
| 2018/0346989 A1* | 12/2018 | Li | C12Q 1/6886 |

FOREIGN PATENT DOCUMENTS

| | | |
|---|---|---|
| CN | 107614686 A | 1/2018 |
| WO | WO-2012078906 A2 | 6/2012 |

OTHER PUBLICATIONS

Manzo et al. Genome Biol., 1478-1 (Year: 2018).*
Laverde et al. J. Biol Chem. 295, 13902-13913 (Year: 2020).*
Liu, Chia-Rung et al.; "Spt4 Is Selectively Required for Transcription of Extended Trinucleotide Repeats"; Cell, Feb. 17, 2012, vol. 148, Issue 4, pp. 690-701, XP-055020434.
Duan, Ranhui et al.; "Towards Understanding RNA-Mediated Neurological Disorders"; Journal of Genetics and Genomics, Elsevier Ltd, Amsterdam, NL, Aug. 24, 2013, vol. 41, Issue 9, pp. 473-484, XP-029071948.
Loomis, Erick W et al.; "Transcription-Associated R-Loop Formation across the Human FMR1 CGG-Repeat Region"; PLOS Genetics, Apr. 17, 2014 vol. 10, Issue 4, e1004294, pp. 1-14, XP-055627235.
Groh, Matthias et al.; "R-loops Associated with Triplet Repeat Expansions Promote Gene Silencing in Friedreich Ataxia and Fragile X Syndrome"; PLOS Genetics, May 2014, vol. 10, Issue 5, e1004318, pp. 1-14, XP-055627237.
Rohilla, K.J. et al. "RNA biology of disease-associated microsatellite repeat expansions"; ACTA Neuropatholgica Communications, Aug. 29, 2017, vol. 5, Issue 63; pp. 1-22; https://doi.org/10.1186/s40478-017-0468-y, XP-021248411.
Boule et al., "The yeast Pif1p DNA helicase preferentially unwinds RNA-DNA substrates", Nucleic Acids Research, 2007, pp. 5809-5818, vol. 35, No. 17.
Cerritelli et al., "Ribonuclease H: the enzymes in eukaryotes", FEBS Journal, 2009, pp. 1494-1505.
Chiang et al.,"Isolation and Characterization of the Human and Mouse Homologues (SUPT4H and Supt4h) of the Yeast SPT4 Gene", Genomics 34, Mar. 1996, pp. 368-375, Article 0299.
Chiang et al.,"Comparison of murine Supt4h and a nearly identical expressed, processed gene: evidence of sequence conservation through gene conversion extending into the untranslated regions" , Nucleic Acids Research, 1998, pp. 4960-4964, vol. 26, No. 21.

(Continued)

*Primary Examiner* — Brian Whiteman
(74) *Attorney, Agent, or Firm* — MUNCY, GEISSLER, OLDS & LOWE, P.C.

(57) ABSTRACT

The present invention provides a method of modulating the expression of a gene containing expanded nucleotide repeats in a cell, comprising: inhibiting the biological activity of SPT4 or SUPT4H; and regulating the formation of R-loops. The inhibition step can effectively reduce the expression of the gene containing the expanded nucleotide repeats and the regulatory step can further enhance the inhibition step. The inhibition step and the regulation step are for the purpose of regulating gene expression by interfering the capacity of RNA polymerase II transcribing over a DNA template with lengthy nucleotide repeats.

12 Claims, 18 Drawing Sheets
Specification includes a Sequence Listing.

(56) References Cited

OTHER PUBLICATIONS

Drolet, "Growth inhibition mediated by excess negative supercoiling: the interplay between transcription elongation, R-loop formation and DNA topology", Molecular Microbiology, Dec. 2006, pp. 723-730, 59(3).

Hartzog et al., "Identification and Analysis of a Functional Human Homolog of the SPT4 Gene of *Saccharomyces* cerevisiae", Molecular and Cellular Biology, Jun. 1996, pp. 2848-2856.

Kim et al., "The sen1+ Gene of *Schizosaccharomyces* pombe, a Homologue of Budding Yeast SEN1, Encodes an RNA and DNA Helicase", Biochemistry, 1999, pp. 14697-14710, 38.

Malone et al., "Molecular and genetic charzterization of SPT4, a gene important for transcription initiation in *Saccharomyces cerevisiae*" MGG, 1993, pp. 449-459, 237.

Mischo et al., "Yeast Sen1 Helicase Protects the Genome from Transcription-Associated Instability", Molecular Cell, 41, Jan. 7, 2011, pp. 21-32, 41, Elsevier Inc.

Sanchez et al., "Characterization of gdp1þ as encoding a GDPase in the ¢ssion yeast *Schizosaccharomyces* pombe". FEMS Microbiology Letters, 2003, pp. 33-38, 228.11.

Scherzinger et al., "Huntingtin-Encoded Polyglutamine Expansions Form Amyloid-like Protein Aggregates In Vitro and In Vivo", Cell, Aug. 8, 1997, pp. 549-558, vol. 90.

Stachora et al., "Human Supt5h protein, a putative modulator of chromatic structure, is reversibly phosphorylated in mitosis", FEBS Letters, 1997, pp. 74-78, 409.13.

Swanson et al., "Isolation of TFC1, a gene encloding one of two DNS-binding subunits of yeast transcription factor (TFIIIC)", Proc. Natl. Aca. Sci, Jun. 1991, pp. 4887-4791, vol. 88.

Tanaka et al., "Trehalose alleviates polyglutamine-mediated pathology in a mouse model of Huntington disease", Nature Medicine, Feb. 2004, pp. 148-154, vol. 10, No. 2.

Zoghbi et al., "Glutamine Repeats and Neurodegeneration", Annu. Rev. Neurosci, 2000, pp. 217-247, 23.

Scherzinger et al., "Self-assembly of polyglutamine-containing huntingtin fragments into amyloid-like fibrils: Implications for Huntington's disease pathology", Proc. Natl. Acad. Sci., Apr. 1999, pp. 4604-4609, vol. 96.

Ning Deng et al., "DSIF modulates RNA polymerase II occupancy according to template G + C content", Jul. 27, 2022 NAR Genomics and Bioinformatics, vol. 4, No. 3, pp. 10.

Hui-Min Cheng et al., "Effects on Murine Behavior and Lifespan of Selectively Decreasing Expression of Mutant Huntingtin Allele by Supt4h Knockdown", Mar. 11, 2015 PLoS Genetics, pp. 17.

Ning Deng et al., Chemical interference with DSIF complex formation lowers synthesis of mutant huntingtin gene products and curtails mutant phenotypes, 2022 PNAS, vol. 119, No. 32, pp. 9.

Nicholas J. Kramer et al., "Spt4 selectively regulates the expression of C9orf72 sense and antisense mutant transcripts", Aug. 12, 2016 Science, vol. 353 Issue 6300.

\* cited by examiner

METHOD TO ENHANCE THE TRANSCRIPTION REGULATION OF SUPT4H ON GENES CONTAINING REPETITIVE NUCLEOTIDE SEQUENCES

CROSS-REFERENCE TO RELATED APPLICATIONS

This is a National Phase Application filed under 35 U.S.C. § 371 as a national stage of PCT/CN2019/072597 filed Jan. 22, 2019, an application claiming the benefit under 35 USC § 119(e) to the following U.S. Provisional Application No. 62/620,308 filed Jan. 22, 2018, the entire contents of each of which are hereby incorporated by reference in their entirety.

The instant application contains a Sequence Listing which has been submitted electronically in the ASCII text file and is hereby incorporated by reference in its entirety. The ASCII text file is a sequence listing entitled "2021-11-30-Seq-Listing" created on Nov. 30, 2021 and having a size of 11,815 bytes in compliance of 37 CFR 1.821.

FIELD OF THE INVENTION

The present invention provides a method of modulating the expression of a gene containing expanded nucleotide repeats in a cell, comprising: inhibiting the biological activity of SPT4 or SUPT4H; and regulating the formation of R-loops. The inhibition step can effectively reduce the expression of the gene containing the expanded nucleotide repeats and the regulatory step can further enhance the inhibition step. The inhibition step and the regulation step are for the purpose of regulating gene expression by interfering the capacity of RNA polymerase II transcribing over a DNA template with lengthy nucleotide repeats.

BACKGROUND OF THE INVENTION

Nucleotide repeat expansion disease comprise a heterogeneous group of diseases that result from instability and expansion of simple tandem repeats (usually tri-nucleotide repeats). Pathogenic expansions can occur in coding or non-coding regions of genes. In disorders such as Friedreich Ataxia, expansions in non-coding regions cause transcriptional silencing or down-regulation of the associated gene and therefore act as recessively inherited, loss-of-function mutations. In contrast, in disorders such as Huntington disease, tri-nucleotide expansions in the protein coding region introduce an abnormally long stretch of a single amino acid (often glutamine) into the associated protein which leads to a dominantly inherited, gain-of function mutation.

Trinucleotide repeat disorders (also known as trinucleotide repeat expansion disorders, triplet repeat expansion disorders or codon reiteration disorders) are a set of genetic disorders caused by trinucleotide repeat expansion, a kind of mutation where trinucleotide repeats in certain genes or introns exceed the normal, stable threshold, which differs per gene. The mutation is a subset of unstable microsatellite repeats that occur throughout all genomic sequences. If the repeat is present in a coding sequence of gene, a dynamic mutation may increase the repeat count and result in a defective gene. If the repeat is present in an intron it can cause toxic effects by forming spherical clusters called RNA foci in cell nuclei. In over half of these disorders, the repeated codon is CAG, which in a coding region, codes for glutamine (Q), resulting in a polyglutamine tract. These diseases are commonly referred to as polyglutamine (or PolyQ) diseases. The remaining disorders repeated codons do not code for glutamine and are classified as non-polyglutamine diseases.

TABLE 1

Non-polyglutamine disease

| Type | Gene | Codon | Normal/wild type | Pathogenic |
| --- | --- | --- | --- | --- |
| FRAXA (Fragile X syndrome) | FMR1, on the X-chromosome | CGG | 6-53 | 230+ |
| FXTAS (Fragile X-associated tremor/ataxia syndrome) | FMR1, on the X-chromosome | CGG | 6-53 | 55-200 |
| FRAXE (Fragile XE mental retardation) | AFF2 or FMR2, on the X-chromosome | CCG | 6-35 | 200+ |
| FRDA (Friedreich's ataxia) | FXN or X25, (frataxin-reduced expression) | GAA | 7-34 | 100+ |
| DM (Myotonic dystrophy) | DMPK | CTG | 5-34 | 50+ |
| SCA8 (Spinocerebellar ataxia Type 8) | OSCA or SCA8 | CTG | 16-37 | 110-250 |
| SCA12 (Spinocerebellar ataxia Type 12) | PPP2R2B or SCA12 | CAG | 7-28 | 66-78 |

Myotonic dystrophy (DM) is the most common adult muscular dystrophy, characterized by autosomal dominant progressive myopathy, myotonia and multiorgan involvement. To date two distinct forms caused by similar mutations have been identified. Myotonic dystrophy type 1 (DM1, Steinert's disease) is caused by a CTG expansion in DMPK, while myotonic dystrophy type 2 (DM2) is caused by a CCTG expansion in CNBP. DM2 is caused by a defect of the CNBP gene on chromosome 3. The specific defect is a repeat of the cytosine-cytosine-thymine-guanosine (CCTG) tetranucleotide in the CNBP gene. As it involves the repeat of four nucleotides, it is not a trinucleotide repeat disorder, but rather a tetranucleotide repeat disorder. The repeat expansion for DM2 is much larger than for DM1, ranging from 75 to over 11,000 repeats.

Moreover, mutations in the C9ORF72 gene were recently identified as the most common cause of ALS and frontotemporal dementia. The pathogenic mechanism in C9ORF72-linked ALS involves the expansion of a non-coding hexanucleotide repeat, GGGGCC, located in an intron of the C9ORF72 gene, from a few repeats in unaffected individuals to hundreds or even thousands of copies in affected individuals.

Spinocerebellar Ataxia Type 10 (SCA10) is characterized by slowly progressive cerebellar ataxia that usually starts as poor balance and unsteady gait, followed by upper-limb ataxia, scanning dysarthria, and dysphagia. Some individuals have cognitive dysfunction, behavioral disturbances, mood disorders, mild pyramidal signs, and peripheral neuropathy. Onset ranges from age 12 to 48 years. Diagnosis of SCA10 is based on clinical findings and confirmed by molecular genetic testing to detect an abnormal ATTCT pentanucleotide repeat expansion in ATXN10, the only gene in which mutation is known to cause the disorder. Affected individuals have expanded alleles with the number of repeats up to 4,500 ATTCT pentanucleotide repeats, although intermediate alleles (280 to 850 repeats) may show reduced penetrance.

Spinocerebellar ataxia type 31 (SCA31) is an adult-onset autosomal-dominant neurodegenerative disorder showing progressive cerebellar ataxia mainly affecting Purkinje cells. Recently, scientist discovered SCA31 mutation as a complex pentanucleotide repeat containing TAAAA, TAGAA, and TGGAA. The size of this repeat ranged from 2.8 to 3.5 kilo-base pairs (kb). Among these repeats, TGGAA repeat appears crucial for SCA31 pathogenesis.

Polyglutamine (PolyQ) diseases are a class of diseases consisting of nine genetically distinct disorders. They include Huntington's disease (HD), dentatorubral-pallidoluysian astrophy (DRPLA), SBMA and spino-cerebellar ataxia 1, 2, 3, 6, 7 and 17 (SCA1/2/3/6/7/17). Because these diseases are caused by the expansion of a translated CAG repeats that codes for the glutamines, they are also known as CAG repeat diseases.

One common physiological characteristic shared among these genetically distinct diseases is that patients who suffer from the diseases are all found to have proteinaceous deposits in their brains. Although in each of these diseases, the proteinaceous deposit is associated with a different protein, the proteins all contain an expanded stretch of glutamines. To date, this expanded stretch of polyQ sequence in the disease-related proteins is the only known genetic mutation implicated in all the polyQ diseases.

In general, the number of CAG repeats in genes can range from a benign number of less than 36 to a pathological number of 37 or more. The larger number of CAG repeats are thought to correlate to pathological phenotypes because proteins and polypeptides that contain a long stretch of glutamines have an inherit propensity to form amyloid-like fibrils (polymerization of protein aggregates with (3-sheet structure) in vitro (Scherzinger et al., 1997), and mutant proteins with an expanded polyQ tract are thought to result in a distinct protein conformation that leads to aggregation and eventual neuronal cell death (Zoghbi and Orr, 2000).

In human, expanded polyQ mutant proteins are expressed widely in cells of the central nervous system (CNS), however, in each different disease, a specific population of neurons is more vulnerable than others. Consequently, the difference in vulnerability results in characteristic patterns of neurodegeneration and clinical features for each of the nine different diseases. The severity of the disease may correlate to the number of CAG repeats. For example, in HD, CAG repeat numbers between 28-35 are considered to be intermediate, 35-40 are considered reduced penetrance, and repeat numbers greater than 40 are considered to be full penetrance.

Table 2 lists eight diseases caused by the expanded CAG repeats, the affected genes, and their defining pathogenic repeat length. SCA6 is not included in this list because unlike other polyQ diseases, the length of CAG repeat in SCA6 is not a determining factor for the age that symptoms begin to present. Pathological repeat length in SCA6 is also much shorter than the other polyQ diseases, where a number between 21-30 is sufficient to cause pathological phenotype.

TABLE 2

| Disease | Gene name/protein product | | Pathogenic repeat length |
|---|---|---|---|
| Spinocerebellar ataxia type 1 | SCA1 | ATXN1/ataxin 1 | 40~82 |
| Spinocerebellar ataxia type 2 | SCA2 | ATXN2/ataxin 2 | 32~200 |
| Spinocerebellar ataxia type 3 | SCA3(MJD) | ATXN3/ataxin 3 | 61~84 |
| Spinocerebellar ataxia type 7 | SCA7 | ATXN7/ataxin 7 | 37~306 |
| Spinocerebellar ataxia type 17 | SCA17 | TBP/TATA box binding protein | 47~63 |
| Dentatorubral pallidoluysian atrophy | DRPLA | ATN1/atrophin 1 | 49~88 |
| Spinal and bular muscular atrophy | SBMA | AR/androgen receptor | 38~62 |
| Huntington's disease | HD | HTT/huntingtin | 40~121 |

Of the above eight diseases, HD is perhaps the most well-known among the general public because of its devastating effects on the patients. The disease is associated with selective neuronal cell death occurring primarily in the cortex and striatum. It is a fatal and cruel disease that progressively deprives the patient of his movement, cognition, and personality, exacting significant economic and emotion tolls on the patient and his family. The frequency of HD is particularly prevalent among people of Western European descent (about 1 in 20,000). Unfortunately, there is presently no cure for this terrible disease.

Currently, available treatments for HD are mainly limited to managing the macroscopic symptoms. For example, one of the newest compound approved by the FDA, tetrabenazine, is a drug for reducing hyperkinetic movements in HD patients. Tetrabenazine is a vesicular monoamine transporter (VMAT) inhibitor which promotes early degradation of neurotransmitters. Thus, the drug merely treats the symptom, not the root of the disease. Other drugs currently used for treating HD include neuroleptics and benzodiazepines. As the disease progresses, an ever wider range of pharmacopeia is needed to address different symptoms, including antipsychotics, and drugs for hypokinesia. No presently known treatment is capable to address the root cause of HD.

As mentioned above, the root cause of HD is an abnormal expansion of CAG repeats in the gene HTT which encodes the protein huntingtin (HTT). In a normal person, there are about 8-25 constitutive repeats of CAG nucleotide sequence in the HTT gene. In a HD patient, the number of CAG repeats are expanded to 36 or more. Because this type of mutation is dominant, a person only needs to inherit one copy of the mutated huntingtin gene to develop HD.

Recent cell and animal model studies have shown that aggregates formed by mutant HTT play a critical role in the progression of HD. It has been observed that the mutant HTT proteins can leave behind shorter fragments from parts of the polyQ expansion when subjected to proteolytic cleavages. If too many copies of glutamine exist in the mutant HTT, the polar nature of glutamine will lead to undesirable interactions with other proteins. In particular, mutant HTT with too many copies of glutamines will form hydrogen bonds with one another and aggregate rather than fold into functional proteins. Over time, the accumulated protein aggregates will damage the neuronal cells, leading to cell death and neurological deficit in the patient. The damaging effects of the protein aggregates have been corroborated by experiments showing that chemical reagents capable of inhibiting the formation of protein aggregates can enhance survival of cells and ameliorate pathology of HD in a mouse model (Sanchez et al., 2003; Tanaka et al., 2004).

Besides using inhibitory molecules to prevent protein aggregation, reducing the expression of mutant huntingtin gene is in principle an alternative way to inhibit the genesis of insoluble protein aggregates. In vitro studies have shown that the extent of polyQ protein aggregation is related to protein concentration (Scherzinger et al., 1999). Therefore, by lowering the level of mutant huntingtin gene expression, a lower level of expanded PolyQ protein will be expressed, which in turn is likely to reduce protein aggregate formation and delay the onset of HD.

These findings point to a potentially simple and powerful strategy of combatting HD pathogenesis by modulating the formation of insoluble protein aggregates resulting from CAG repeat mutation in HTT. For example, a therapeutic agent that can modulate the expression of the polyQ mutant genes or formation of the polyQ aggregates can potentially address the root cause of the polyQ diseases, not just their physiological symptoms. Unfortunately, the lack of knowledge about cellular factors and agents that can modulate the expression of the mutant polyQ genes has prevented practical development of this therapeutic strategy.

Polyglutamine (polyQ) diseases are dominant neurological disorders, caused by abnormal CAG tri-nucleotide expansion in the coding sequence of affected genes. Extension of CAG repeats results in the production of aberrant gene products that are deleterious to neurons. It is thus of great interest and importance to develop methods preventing or eliminating the production of mutant gene products. In our earlier studies, we found that the transcript production of genes containing lengthy CAG repeats is preferentially suppressed by a deficiency of transcription elongation factor SPT4/SUPT4H. However, the underlying mechanism accounting for the requirement of SPT4/SUPT4H in the process of transcription elongation over DNA templates containing lengthy repetitive nucleotide sequences is still elusive.

R-loop, a nucleic acid structure comprising of nascent mRNA and transcribed DNA segment behind transcription mechinery, is a by-product of transcription elongation and has been demonstrated as a negative regulator of gene expression.

Cells bear a number of regulatory proteins to remove RNA/DNA hybrids (R-loops). The most well characterized ones are RNase H enzymes, which specifically cleave the RNA moiety of the RNA/DNA hybrid (Cerritelli and Crouch, 2009). Additionally, R-loop removal can be achieved through the action of helicase. In eukaryotes, RNA/DNA hybrids can be unwound by Pif1 DNA helicase (Boule and Zakian, 2007) or Sen1/Senataxin (Kim et al., 1999). It was proposed that a key function of yeast Sen1 is to prevent R-loop accumulation (Mischo et al., 2011). Topoisomerase I also plays an important role in preventing transcription-coupled R-loop formation (Drolet, 2006).

SUMMARY OF THE INVENTION

Definitions

Throughout this disclosure, gene names are denoted with capital letters, and the proteins associated with the genes only in yeast cells are denoted in letters with the first letter capitalized. For example, for the SPT4 gene, the term "SPT4" denotes the gene and the term "Spt4" denotes the protein produced by the gene.

As used herein, the gene SPT4 refers to the gene that encodes the transcription elongation protein Spt4. The gene is characterized by (Malone et al., 1993), the entire content of which is incorporated herein by reference. The protein Spt4 is characterized by (Malone et al., 1993), the entire content of which is incorporated herein by reference.

As used herein, the gene SPT5 refers to the gene that encodes the transcription elongation protein Spt5. The gene is characterized by (Swanson et al., 1991), the entire content of which is incorporated herein by reference. The protein Spt5 is characterized by (Swanson et al., 1991), the entire content of which is incorporated herein by reference.

As used herein, the gene SUPT4H refers to the gene that encodes the mammalian transcription elongation factor SUPT4H. The gene is characterized by (Hartzog et al., 1996; Chiang et al., 1996), the entire content of which is incorporated herein by reference. The protein SUPT4H is characterized by (Hartzog et al., 1996; Chiang et al., 1996), the entire content of which is incorporated herein by reference.

As used herein, the gene SUPT5H refers to the gene that encodes the mammalian transcription elongation factor SUPT5H. The gene is characterized by (Stachora et al., 1997; Chiang et al., 1998), the entire content of which is incorporated herein by reference. The protein SUPT5H is characterized by (Stachora et al., 1997; Chiang et al., 1998), the entire content of which is incorporated herein by reference.

The term "R-loop stabilizing compound" as used herein describe any compound with the capability of stabilizing or preserving R-loop structure. e.g., inhibitors of RNase H, TOP1, SEN1.

The term "biological function" as used herein describe the function of assisting RNA polymerase II transcribing over DNA template via Spt4 or SUPT4H and/or its binding partner Spt5 or SUPT5H.

The term "gene products" as used herein describe RNAs and proteins produced from the gene.

RNA/DNA hybrids (R-loops) are detectable in expanded CAG tri-nucleotide repeats.

R-loops also occur in a variety of repetitive DNA sequences.

SPT4 deficiency does not affect R-loop formation, but results in a sub-optimized RNA polymerase II that is sensitive to the transcriptional stalling effect of R-loops.

Elevation of R-loop augments the transcriptional reduction of mutant HTT by SUPT4H inactivation, suggesting the potential of targeting SUPT4H and RNase H together to against Huntington's disease (HD).

In one aspect, using yeast as a model system, we found that R-loops are detectable in the vicinity of DNA segments containing lengthy CAG tri-nucleotide repeats and other repetitive nucleotide sequences. In addition, we found that the greater number of repeating units has a higher probability of R-loop formation. We further revealed that R-loops are not affected by the presence or absence of SPT4; however, transcription-coupled R-loops in the genes containing lengthy nucleotide repeats attribute and modulate the level of transcription reduction by Spt4 deficiency. More importantly, the action of mechanism revealing in model yeast system is also applicable to mutant HTT gene in mouse striatal neurons as well as to HD animals.

In one aspect, described herein is a method of modulating the expression of a gene containing expanded nucleotide repeats in a cell, comprising: inhibiting biological function of SPT4 or SUPT4H; and modulating formation of R-loops.

In some embodiments, the inhibiting step has an ability to reduce the expression of gene products from the gene containing expanded nucleotide repeats and the modulating step potentiate the ability.

In some embodiments, the inhibiting step is performed by a gene suppressing method selected from the group of siRNA, shRNA, anti-sense oligonucleotide and CRISPR/Cas9 technology to against SPT4 or SUPT4H.

In some embodiments, the inhibiting step disrupting formation of an Spt4/Spt5 complex or an SUPT4H/SUPT5H complex.

In some embodiments, the inhibiting step and the modulating step trigger dissociation of RNA polymerase II from the DNA template, and modulate the expression of the gene.

In some embodiments, the gene contains a segment of DNA with repetitive nucleotide sequences that are prone to R-loop formation.

In some embodiments, the gene contains expanded tri-nucleotide repeats.

In one aspect, provided herein a method of inhibiting the transcription of a gene containing expanded nucleotide repeats in a cell, comprising: administering a SPT4 or SUPT4H inhibiting compound; and a R-loop regulating compound in the cell.

In some embodiments, the R-loop regulating compound is selected from a group consist of a R-loop stabilizing compound and a RNase H inhibitor.

In some embodiments, the R-loop stabilizing compound potentiates R-loop formation or prevents the resolution of existing R-loops.

In some embodiments, the RNase H inhibitor inhibits RNase H enzymatic activity and prevents its function on resolution of R-loops.

In some embodiments, the SPT4 or SUPT4H inhibiting compound is an antibody, a chemical reagent, a peptide, or a nucleic acid reagent, which suppresses SPT4 or SUPT4H expression or inhibits formation of an Spt4/Spt5 complex or an SUPT4H/SUPT5H complex.

In some embodiments, the R-loop regulating compound is an antibody, a chemical reagent, a peptide, or a nucleic acid reagent.

In some embodiments, the gene contains a segment of DNA with repetitive nucleotide sequences that are prone to R-loop formation.

In some embodiments, the gene contains expanded tri-nucleotide repeats.

In one aspect, provided herein a pharmaceutical composition for treating a nucleotide repeat expansion disease, comprising: a R-loop regulating compound and a SPT4 or SUPT4H inhibiting compound.

In some embodiments, the R-loop regulating compound is selected from a group consist of a R-loop stabilizing compound and a RNase H inhibitor.

In some embodiments, the R-loop stabilizing compound is Topoisomerase inhibitors.

In some embodiments, the RNase H inhibitor is Tropolone.

In some embodiments, the SPT4 or SUPT4H inhibiting compound is an antibody, a chemical reagent, a peptide, or a nucleic acid reagent.

In some embodiments, the R-loop regulating compound is an antibody, a chemical reagent, a peptide, or a nucleic acid reagent.

In one aspect, provided herein a method of enhancing drug therapy of nucleotide repeat expansion disease in a subject, wherein the method comprising administering to said subject a R-loop regulating compound with a nucleotide repeat expansion disease drug.

In some embodiments, the nucleotide repeat expansion disease drug is a SPT4 or SUPT4H inhibiting compound.

In some embodiments, the R-loop regulating compound is an antibody, a chemical reagent, a peptide, or a nucleic acid reagent.

In some embodiments, the nucleotide repeat expansion disease is selected from the group consisting of spinocerebellar ataxia type 1, 2, 3, 7, 17, dentatorubral-pallidoluysian atrophy, spinal bulbar muscular atrophy, myotonic atrophy type 1, 2, C9orf72 amyotrophic lateral sclerosis, Spinocerebellar ataxia Type 8, Spinocerebellar ataxia Type 10, Spinocerebellar ataxia Type 12, Spinocerebellar ataxia Type 31, Spinocerebellar ataxia Type 36 and Huntington's disease.

The details of one or more embodiments are set forth in the accompanying drawing and the description below. Other features, objects, and advantages of the embodiments will be apparent from the description and drawing, and from the claims.

DETAILED DESCRIPTION OF THE INVENTION

Figure 1:
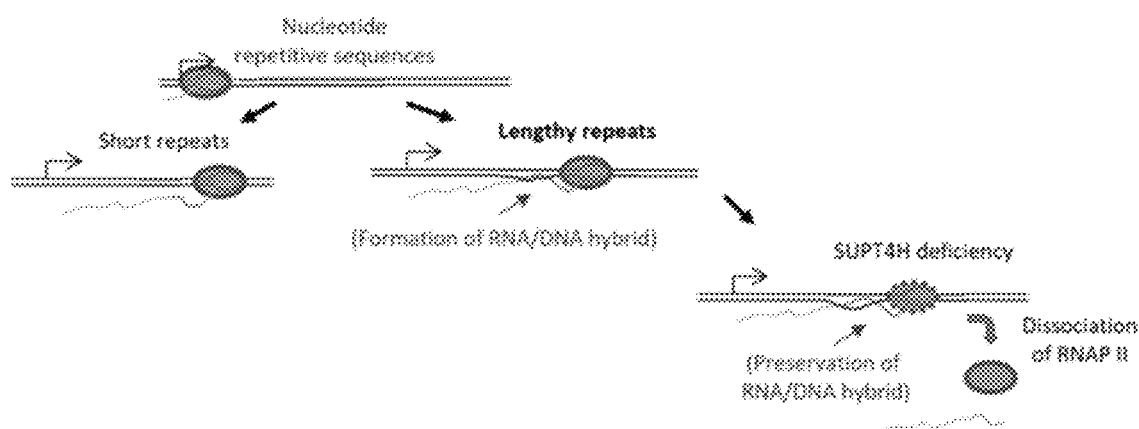
FIG. 1 is a Graphic illustration of the process of transcription elongation on genes containing either a stretch of short or lengthy repetitive nucleotide sequences.
Figure 2A:
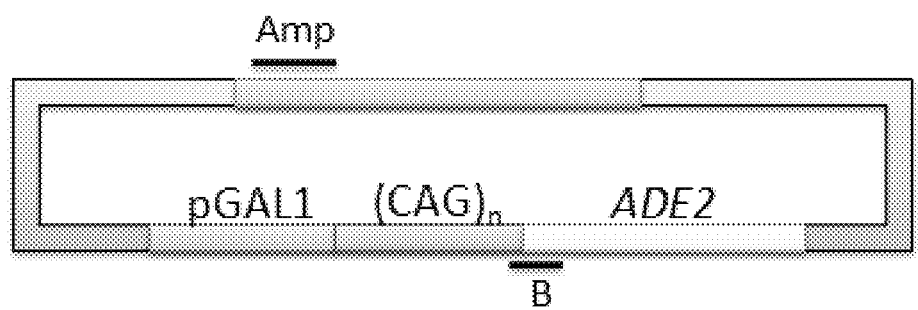
FIG. 2A is a schematic diagram that shows the amplicons by primer set B and primer set Amp on (CAG)n-ADE2 plasmid.
Figure 2B:
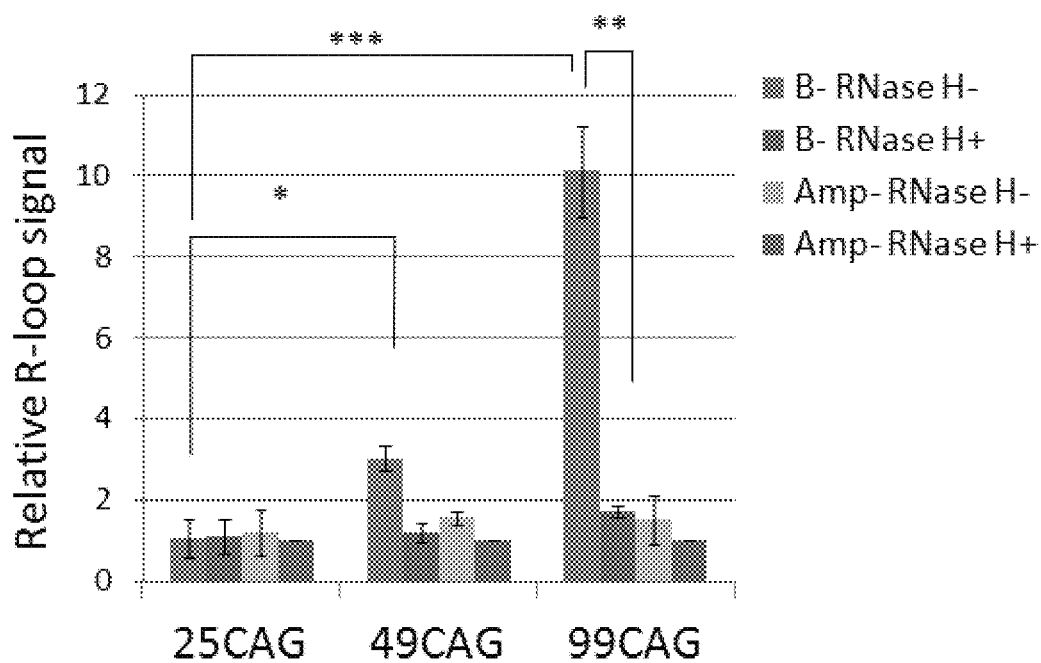
FIG. 2B is a bar graph that shows analysis of R-loop signal on transcribed (CAG)n-ADE2 by RNA/DNA hybrid precipitation (DIP) method.
Figure 2C:
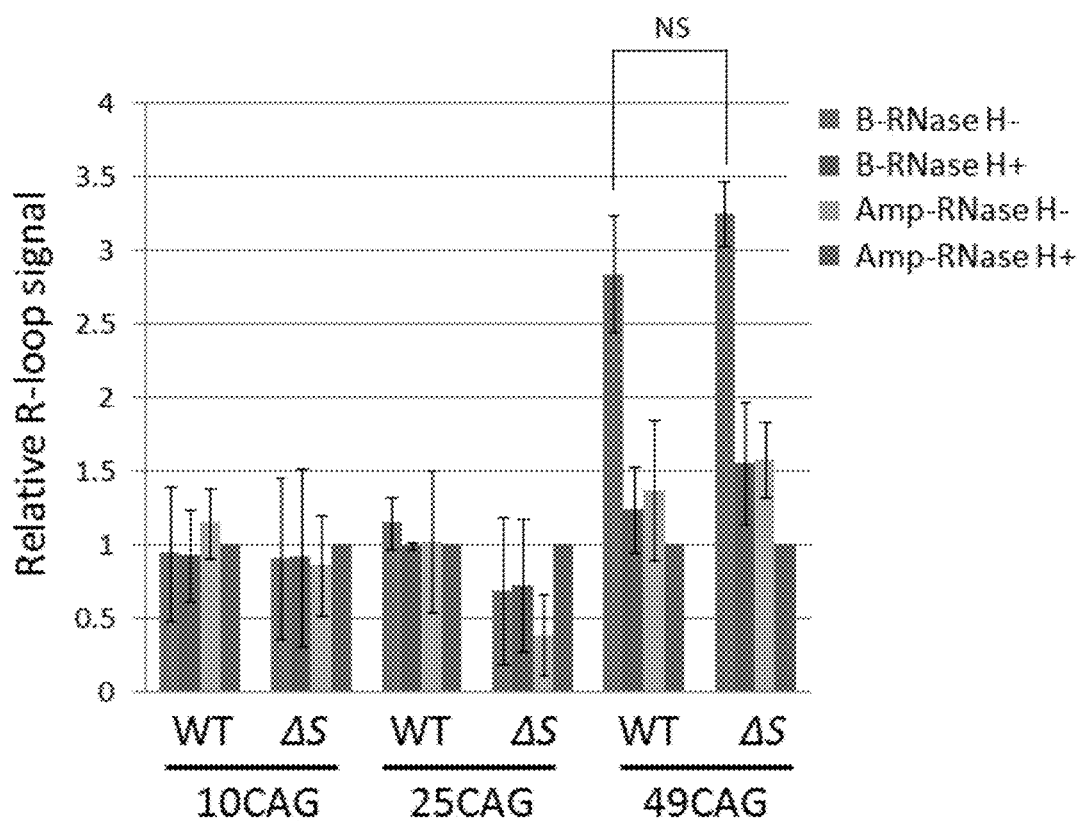
FIG. 2C is a bar graph that shows examination of the effect of Spt4 deficiency on the formation of R-loops.
Figure 2D:
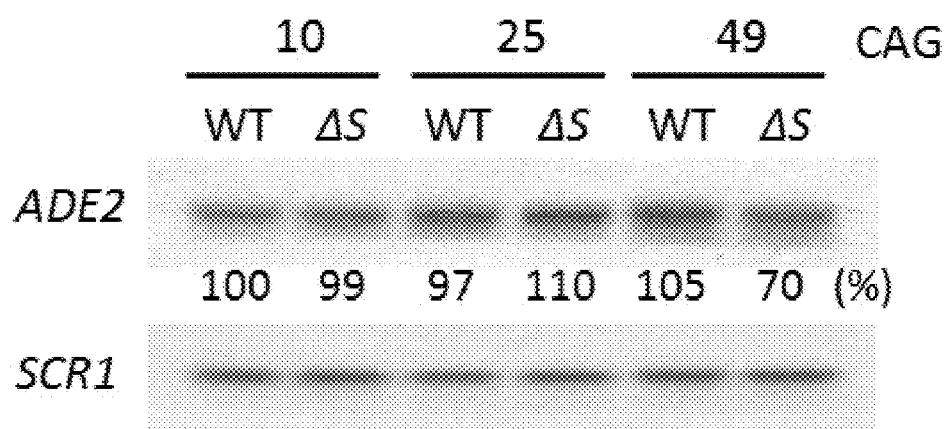
FIG. 2D is a graph that shows assessment of (CAG)n-ADE2 mRNA expression by Northern blotting in wild-type (WT) and SPT4Δ (ΔS) cells.
Figure 3A:
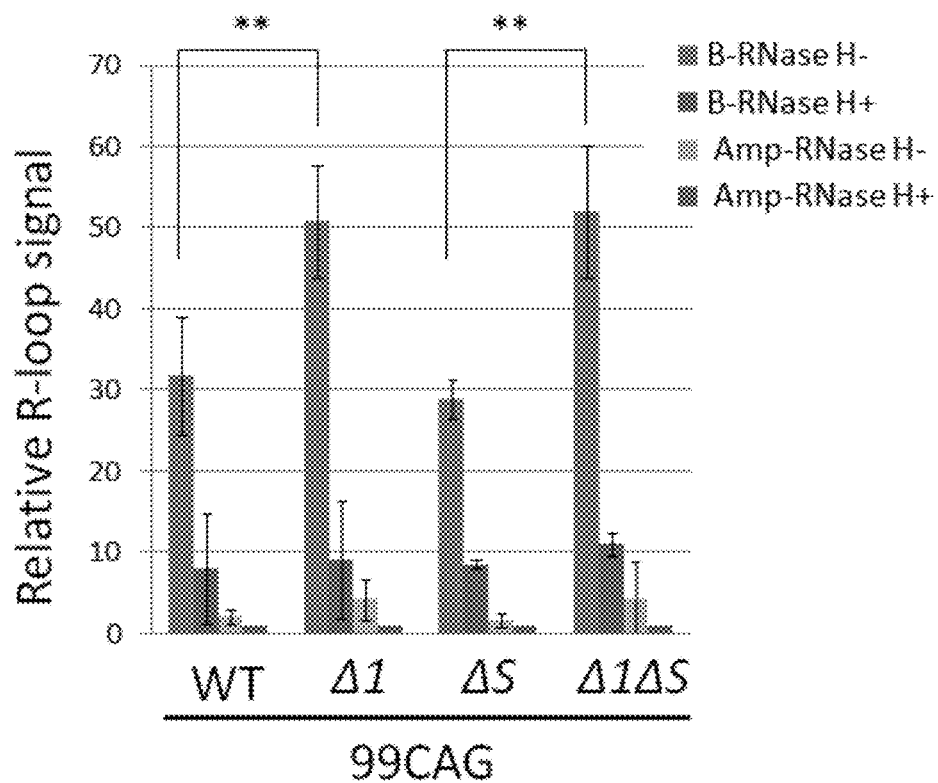
FIG. 3A is a bar graph that shows analysis of R-loop signal in wild-type (WT), RNH1Δ (Δ1), SPT4Δ (ΔS) and RNH1Δ SPT4Δ double deletion (ΔLΔS) cells.
Figure 3B:
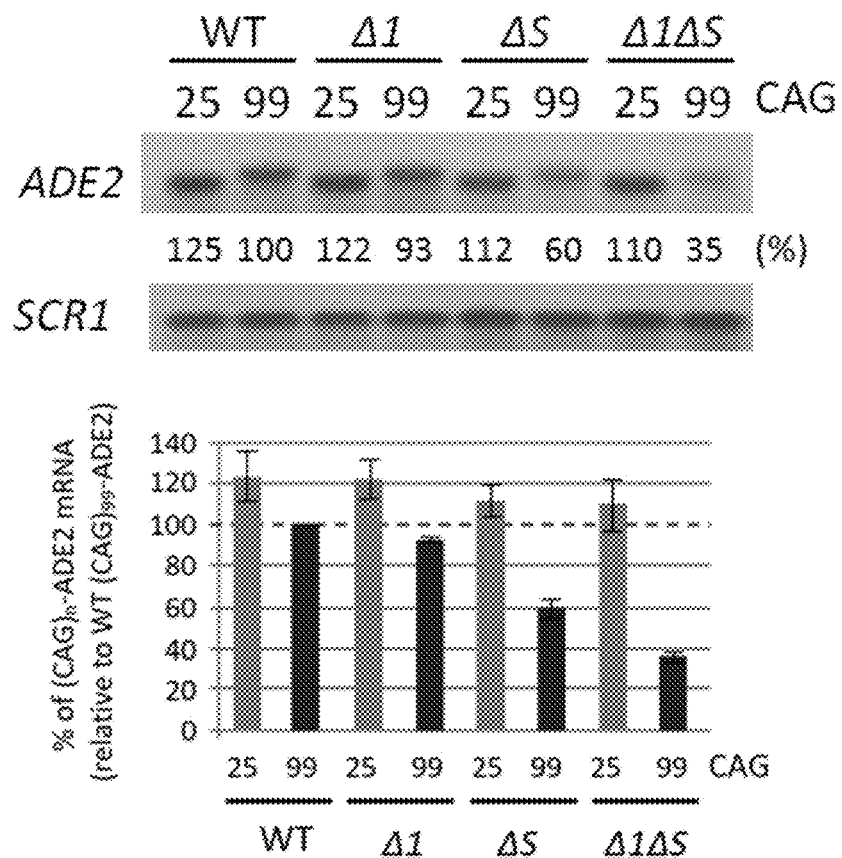
FIG. 3B is a graph that shows measurement of (CAG)n-ADE2 mRNA expression by Northern blotting in WT, Δ1, ΔS and Δ1ΔS cells.
Figure 3C:
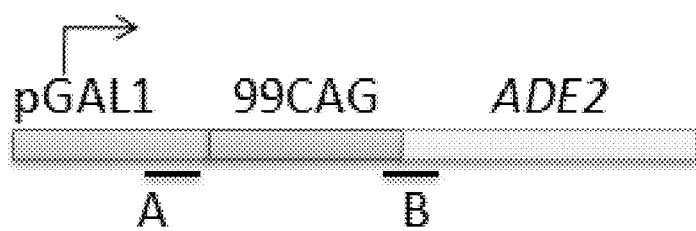
FIG. 3C is a schematic diagram that shows the amplicons by primer sets A and B.
Figure 3D:
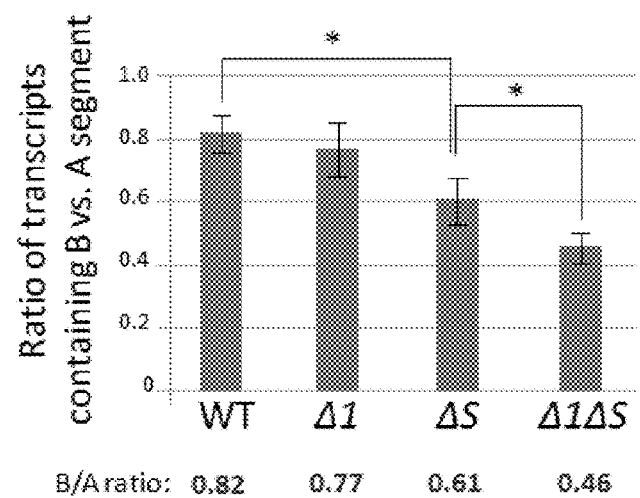
FIG. 3D is a bar graph that shows analysis of transcripts with downstream vs. upstream of CAG repeats by reverse transcription and real-time quantitative PCR.
Figure 4A:
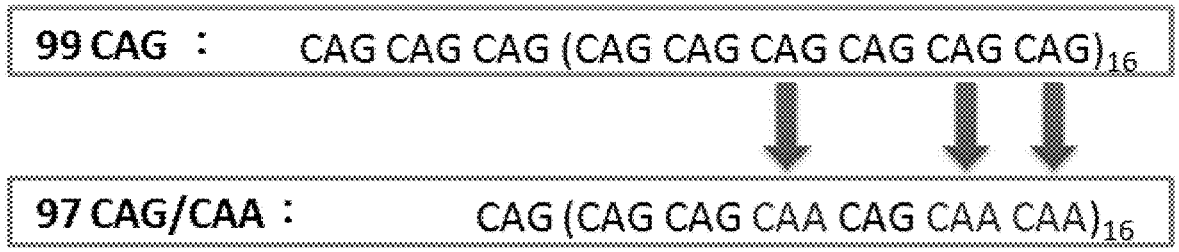
FIG. 4A is a schematic diagram that shows the difference between 99 CAG (SEQ ID NO: 44) and 97 CAG/CAA (SEQ ID NO: 45) in nucleotide sequence composition.
Figure 4B:
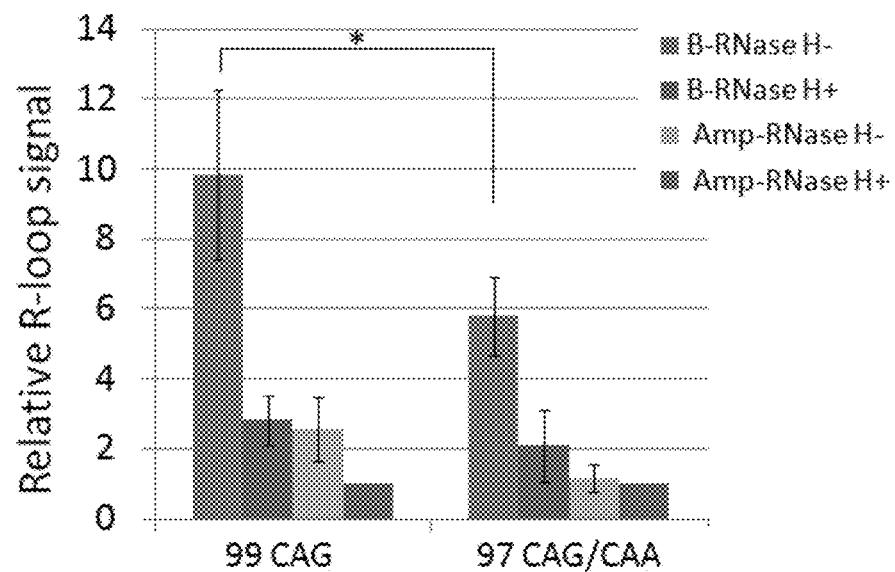
FIG. 4B is a bar graph that shows analysis of R-loop signal in repetitive sequences by DIP assay in WT cells expressing $(CAG)_{99}$-ADE2 and $(CAG/CAA)_{97}$-ADE2.
Figure 4C:
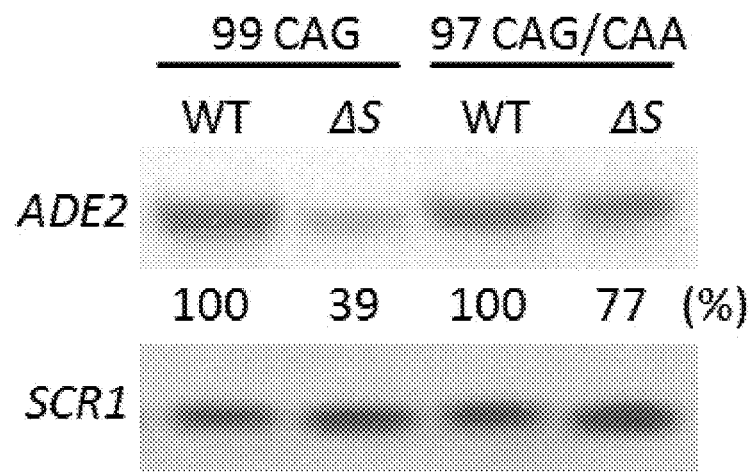
FIG. 4C is a graph that shows assessment of $(CAG)_{99}$-ADE2 and $(CAG/CAA)_{97}$-ADE2 expression by Northern blotting in wild-type (WT) and SPT4Δ (ΔS) cells.
Figure 4D:
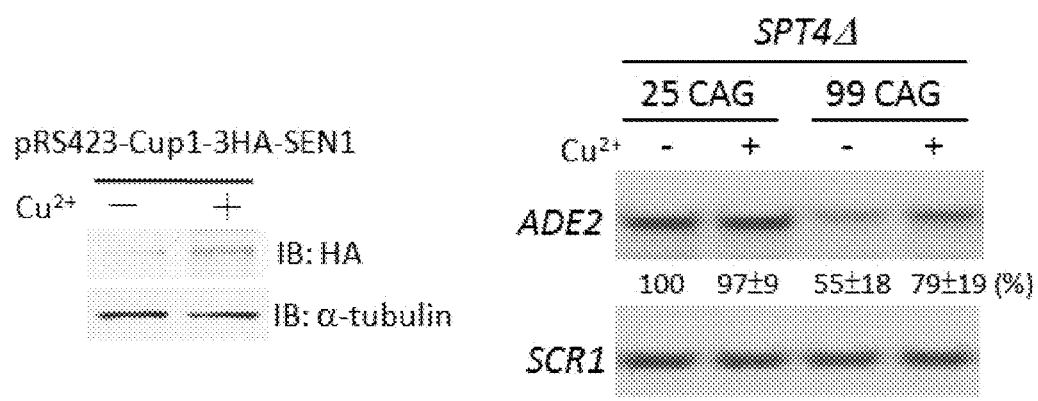
FIG. 4D is a graph that shows measurement of (CAG)n-ADE2 mRNA abundance by Northern blotting in SPT4Δ cells expressing ectopic SEN1.
Figure 4E:
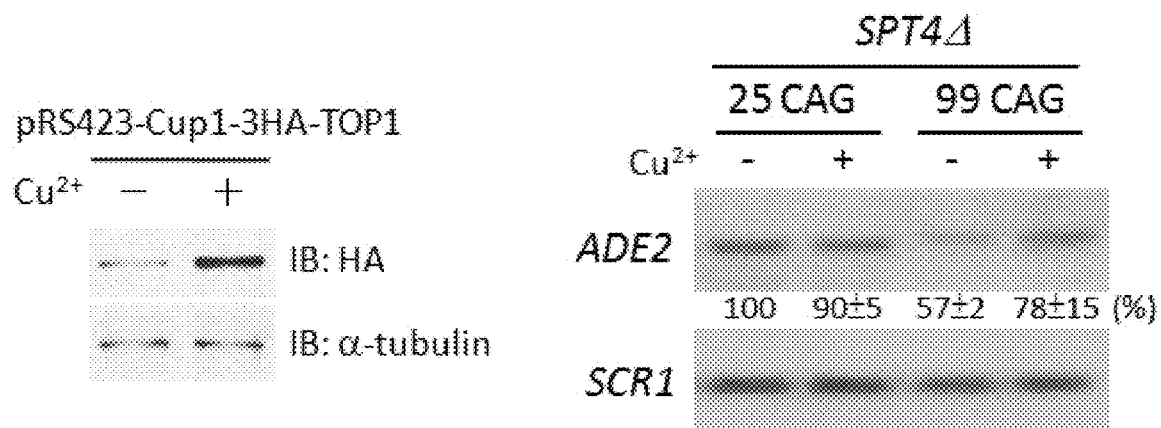
FIG. 4E is a graph that shows measurement of (CAG)n-ADE2 mRNA abundance by Northern blotting in SPT4Δ cells expressing ectopic TOP1.
Figure 5A:
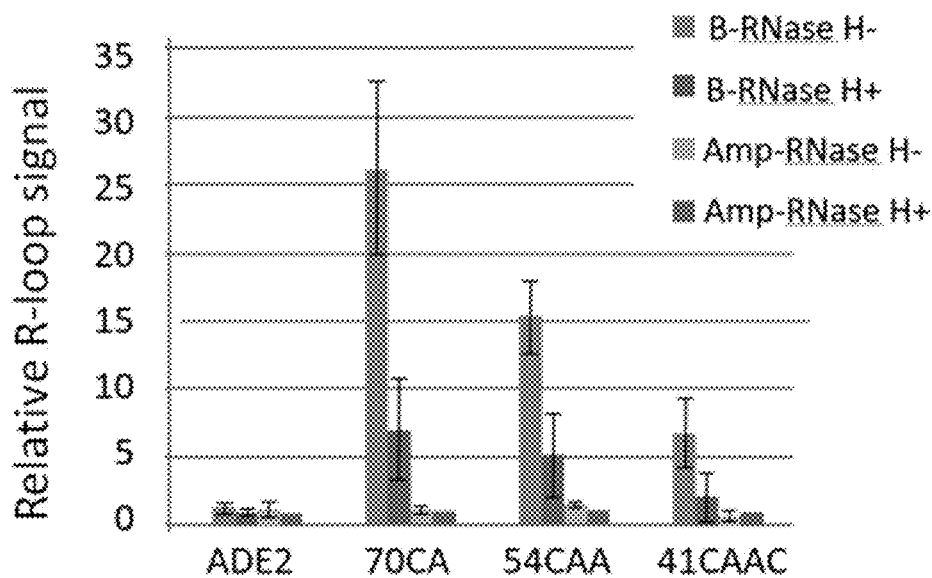
FIG. 5A is a bar graph that shows analysis of R-loop signal by DIP assay in WT cells expressing ADE2 reporter gene with none, 70 CA, 54 CAA, or 41 CAAC repeats.
Figure 5B:
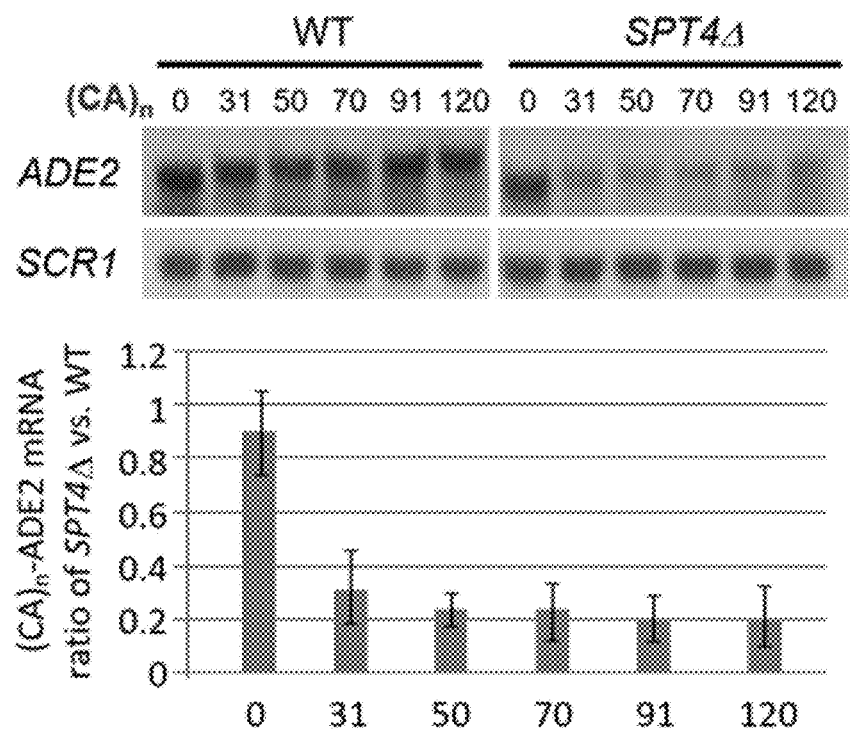
FIG. 5B is a graph that shows assessment of $(CA)_n$-ADE2 expression by Northern blotting in wild-type (WT) and SPT4Δ cells.
Figure 5C:
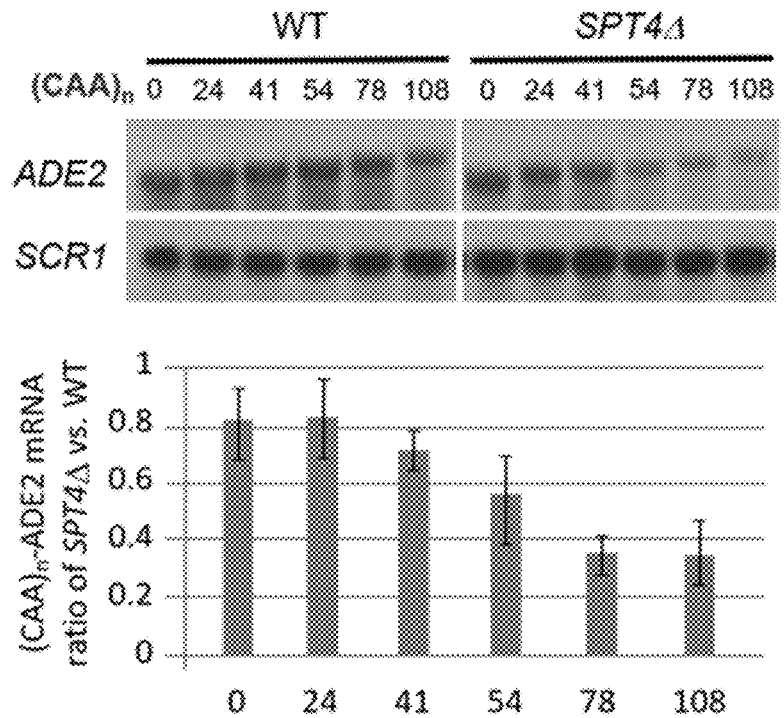
FIG. 5C is a graph that shows assessment of (CAA)$_n$-ADE2 expression by Northern blotting in wild-type (WT) and SPT4Δ cells.
Figure 5D:
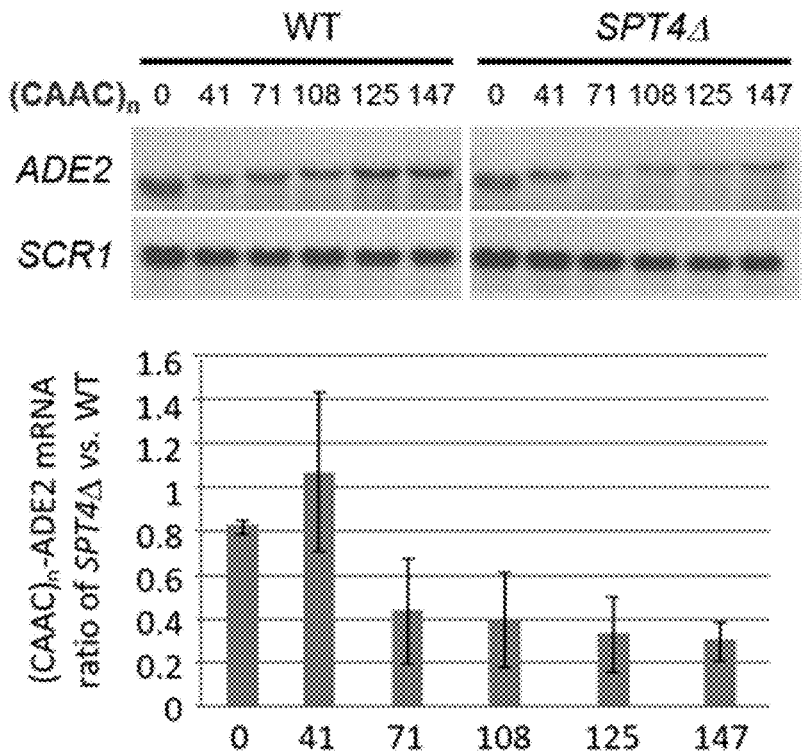
FIG. 5D is a graph that shows assessment of (CAAC)$_n$-ADE2 expression by Northern blotting in wild-type (WT) and SPT4Δ cells.
Figure 5E:
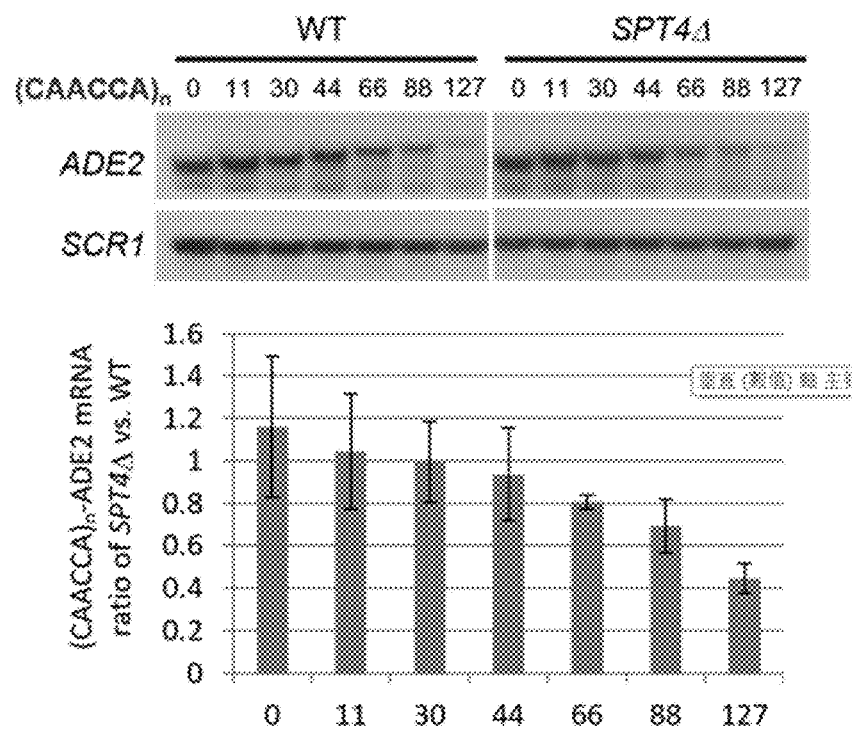
FIG. 5E is a graph that shows assessment of (CAACCA)$_n$-ADE2 expression by Northern blotting in wild-type (WT) and SPT4Δ cells.

Please refer to FIG. 1. Graphic illustration of the process of transcription elongation on genes containing either a stretch of short or lengthy repetitive nucleotide sequences. Transcription-mediated RNA/DNA hybrid (R-loop) formation occurs in DNA templates with lengthy repeats, which could result in a stall of RNA polymerase II (RNAP II) on transcribed template. When cells are deficient in SPT4 (in yeast) or SUPT4H (in mammals), the processivity of RNAP II is sub-optimal and the transcription machinery is prone to dissociate from DNA template due to the stalling effect of R-loops. SPT4/SUPT4H does not affect R-loop formation on DNA templates with lengthy repeats. However, the transcription reduction of genes containing a long stretch of repetitive sequences is modulated by the level of R-loops on transcribed templates in SUPT4H deficient cells. Blue ovals represent RNA polymerase II (RNAP II) and nucleotide repetitive sequences are indicated as red line segment.

Example 1: Material and Method

Yeast Strains and Plasmids

All deletion strains were created by one-step gene replacement method and confirmed by PCR as previously described (Liu et al., 2012). SPT4Δ and RNH1Δ strains were derived from W303-1A cells by replacing the corresponding ORFs with KanMX and NatMX antibiotic selection cassette respectively.

Plasmid constructs that possess a variety of repetitive nucleotide sequences, including CA, CAA, CAG, CAAC, and CAACCA in different repeating units were generated by a methodology described previously (Liu et al., 2012). Full-length TOP1 coding sequence and the N-terminal portion of SEN1 (encoding amino acid residue 1 to 1017) were amplified by PCR using yeast genomic DNA as a template. The amplicons of TOP1 (by SmaI-TOP1 F and TOP1-NotI R primers) and SEN1 (by SmaI-SEN1 F and SEN1-NotI R primers) were cloned into vector pRS423-Cup1-3HA to generate pRS423-Cup1-TOP1 and pRS423-Cup1-SEN1 respectively.

Antibodies

S9.6, a monoclonal antibody that specifically recognizes RNA/DNA hybrid structure, was generously provided by Dr. Stephen H. Leppla (NIAID, National Institutes of Health). Antibodies against α-Tubulin (DM1A, Sigma), HA-epitope (3F10, Roche), SUPT4H (64828, Cell Signaling Technology), Huntingtin (MAB2166, Chemicon), TATA-box binding protein (58C6, Sigma) were purchased.

RNA/DNA Immunoprecipitation (DIP) Assay

Yeast cells were collected after culturing in 2% galactose-containing medium for 12 hours, and then grinded by glass beads in the presence of 300 μl extraction buffer (10 mM Tris-HCl pH 8.0, 10 mM EDTA, 200 mM NaCl, 1% SDS, 2% Triton X-100, 25 units RNase inhibitor). The nucleic acid mixture was subjected to sonication (Bioruptor UCD-200) and extracted by phenol (pH 8.0). Purified chromatin DNA and RNA, with or without RNase H treatment for 90 minutes, was precipitated by monoclonal antibody S9.6 bound to protein G agarose beads. The precipitate was washed with four different washing buffers (Washing buffer 1: mM HEPES-KOH pH 7.5, 50 mM NaCl, 1 mM EDTA, 1% Triton X-100, 0.2% SDS; Washing buffer 2: 50 mM HEPES-KOH pH 7.5, 500 mM NaCl, 1 mM EDTA, 1% Triton X-100, sodium deoxycholate; Washing buffer 3: 10 mM Tris-HCl pH 8.0, 250 mM LiCl, 1 mM EDTA, 0.5% NP-40, 0.5% sodium deoxycholate; Washing buffer 4: TE buffer) two times and then extracted again by phenol. The RNA/DNA hybrid (R-loop) signal was analyzed by qPCR and the Quantitative-Comparative CT (MCT) program. In yeast experiments, a pair of primers (Primer-B F and Primer-B R) were used to quantify R-loop signal in the vicinity of CAG repeats and the primer set AMP was used as a control. Alternatively, Primer-B' F and Primer-B R were employed to detect R-loops for CAG and non-CAG repetitive sequences. In ST14A, primer set ST14A eGFP was used to detect R-loop signal and primer set AMP served as control. For Hdh$^{Q7/Q7}$ and Hdh$^{Q111/Q111}$, mouse HTT DIP primer set was used to quantify R-loop signal of the CAG repeating region and Tubal a DIP primer set was included as a control.

Northern Blotting

Total RNA was extracted from yeast cells using hot acid phenol method (Liu et al., 2012). Equivalent amounts of RNA were loaded and separated on 1% agarose gels with 1% formaldehyde in MOPS buffer, and then transferred to Nylon membrane (PerkinElmer). The membranes were then hybridized with ADE2 probe to detect the transcript of report genes containing none or varied length of nucleotide repetitive sequences. SCR1 was included and served as a loading control. ADE2 and SCR1 probes were synthesized by a pair of ADE2-F and ADE2-R primers and a set of SCR1-F and SCR1-R primers as per manufacturer's instruction (DIG Northern Starter Kit, Roche).

Mammalian Cell Culture and Transfection

ST14A, Hdh$^{Q7/Q7}$ and Hdh$^{Q111/Q111}$ were maintained in DMEM (HyClone) supplemented with 15% fetal bovine serum at 33° C. with 5% CO$_2$. ST14A$^{tet}$ is a genetic engineered stable line, which integrated pTet-Off construct in the genome of ST14A cells and could trigger the expression of pTRE2-(CAG)n-eGFP plasmid in the absence of tetracycline. Lipofectamine 2000 (Invitrogen) transfection reagent was used to deliver siRNA or together with pTRE2-(CAG)n-eGFP into cells. 100 nM of SUPT4H siRNA (DHARMACON, ON-TARGET plus SMART pool, L-048866-01) and (DHARMACON, J-086342-10, 5'-UGGCCUACAAAUCGAGAGAUU-3' (SEQ ID NO: 1) and 5'-UCUCUCGAUUUGUAGGCCAUU-(SEQ ID NO: 2)) were used to knock-down SUPT4H expression in mice and rat cells, respectively.

Microscopy

ST14A$^{tet}$ cells were co-transfected with pTRE2-(CAG)n-eGFP plasmid and siRNA. 6 hours post-transfection, the growth medium was changed to DMEM for cell incubation of 12 hours. After incubation, cells were treated with or without 60 μM Tropolone (T89702, Sigma) for another 12 hours. GFP signals were then visualized using Nikon TS100 fluorescence microscope and images were taken by Nikon D5200 camera.

Reverse Transcription (RT) and Quantitative PCR (qPCR)

For mammalian cells, total RNA was isolated using TRIzol reagent as per manufacturer's instruction (Invitrogen). 2 μg total RNA was reverse transcribed into cDNA using SuperScript III reverse transcriptase (Invitrogen) together with oligo dT and snRNA U6 rt primers. The amount of cDNAs were quantified by StepOnePlus Real-Time qPCR system (Applied Biosystems) and analyzed by the Quantitative-Comparative CT (ΔΔCT) program. Rat SUPT4H, eGFP, mouse SUPT4H, and Mouse HTT were measured using corresponding primer sets as indicated in TABLE 3. snRNA U6 was included as a loading control.

TABLE 3 oligonucleotide primers used in this disclosure:

| Northern blot probes | Sequence |
|---|---|
| ADE2-F primer | 5'-TCCGGAAGCTTTGGAAGTACTG-3'(SEQ ID NO: 3) |
| ADE2-R primer | 5'-TAAGTTGAACGGAGTCCGGAAC-3' (SEQ ID NO: 4) |
| SCR1-F primer | 5'-GGCTGTAATGGCTTTCTGGTG-3'(SEQ ID NO: 5) |
| SCR1-R primer | 5'-ACCAGACAGAGAGACGGATTC-3'(SEQ ID NO: 6) |
| DIP for yeast | Sequence |
| Primer-B F primer | 5'-CAGCAGCAGGGGGGATCCGATTC-3'(SEQ ID NO: 7) |
| Primer-B' F primer | 5'-CGGGATCCATGGATTCTAGAACAGTTGGT-3'(SEQ ID NO: 8) |
| Primer-B R primer | 5'-TCAGCTAGTTTTTCGATATCAAGAGG-3' (SEQ ID NO: 9) |
| AMP F primer | 5'-TTAATCAGTGAGGCACCTATC-3'(SEQ ID NO: 10) |
| AMP R primer | 5'-ATCATGTAACTCGCCTTGATC-3'(SEQ ID NO: 11) |
| DIP for mammalian cells | Sequence |
| ST14A eGFP F primer | 5'-CTGAACTTGTGGCCGTTTACGTCG-3'(SEQ ID NO: 12) |
| ST14A eGFP R primer | 5'-TCCCCCCGGGATGGTGAGCAAGGGCGAGG-3'(SEQ ID NO: 13) |
| AMP F primer | 5'-TTAATCAGTGAGGCACCTATC-3'(SEQ ID NO: 14) |
| AMP R primer | 5'-ATCATGTAACTCGCCTTGATC-3'(SEQ ID NO: 15) |
| Mouse HTT DIP F primer | 5'-CGCCTCCTCAGCTTCCTCAG-3'(SEQ ID NO: 16) |
| Mouse HTT DIP R primer | 5'-GGTTGCTGGGTCACTCTGTC-3'(SEQ ID NO: 17) |
| Mouse Tuba1 a DIP F primer | 5'-CCATTGGCAAGGAGATCATTG-3'(SEQ ID NO: 18) |
| Mouse Tuba1 a DIP R primer | 5'-ATGGCCTCATTGTCTACCATG-3'(SEQ ID NO: 19) |
| RT and qPCR for yeast | Sequence |
| 5' end CAG rt primer | 5'-CTGCTGCTGCTGCTGCTG-3'(SEQ ID NO: 20) |
| 3' end CAG rt primer | 5'-TAAGTTGAACGGAGTCCGGAAC-3' (SEQ ID NO: 21) |
| SCR1 rt primer | 5'-ACCAGACAGAGAGACGGATTC-3'(SEQ ID NO: 22) |
| 5' CAG F primer | 5'-ACTACAAGGACGACGATGAC-3'(SEQ ID NO: 23) |
| 5' CAG R primer | 5'-CTGCTGCTGGGGTTTGAGGG-3'(SEQ ID NO: 24) |
| 3' CAG F primer | 5'-CAGCAGCAGGGGGGATCCGATTC-3(SEQ ID NO: 25)' |
| 3' CAG R primer | 5'-TCAGCTAGTTTTTCGATATCAAGAGG-3'(SEQ ID NO: 26) |
| SCR1 F primer | 5'-GGCTGTAATGGCTTTCTGGTG-3'(SEQ ID NO: 27) |
| SCR1 R primer | 5'-ACCAGACAGAGAGACGGATTC-3'(SEQ ID NO: 28) |
| RT and qPCR for mammalian cells | Sequence |
| snRNA U6 rt primer | 5'-AAAAATATGGAACGCTTCACGA-3'(SEQ ID NO: 29) |
| snRNA U6 F primer | 5'-CTCGCTTCGGCAGCACATAT-3'(SEQ ID NO: 30) |
| snRNA U6 R primer | 5'-TATGGAACGCTTCACGAATTTG-3'(SEQ ID NO: 31) |
| rat SUPT4H F primer | 5'-CCTGGTGTACCCTCCTTTGA-3'(SEQ ID NO: 32) |
| rat SUPT4H R primer | 5'-ATTACCCATGGCTCCCTTCT-3'(SEQ ID NO: 33) |
| eGFP F primer | 5'-CTGAACTTGTGGCCGTTTACGTCG-3'(SEQ ID NO: 34) |
| eGFP R primer | 5'-TCCCCCCGGGATGGTGAGCAAGGGCGAGG-3'(SEQ ID NO: 35) |
| Mouse SUPT4H F primer | 5'-TCATTGCGATGATGAGTCCAG-3'(SEQ ID NO: 36) |
| Mouse SUPT4H R primer | 5'- TTTCGTGGAGTCTGCTGATTC-3'(SEQ ID NO: 37) |
| Mouse HTT F primer | 5'-TCCTGATCAGTGAAGTGGTTC-3'(SEQ ID NO: 38) |
| Mouse HTT R primer | 5'-GTCACACTCCAACACATAGAG-3'(SEQ ID NO: 39) |

TABLE 3-continued oligonucleotide primers used in this disclosure:

| Cloning primers | Sequence |
| --- | --- |
| SmaI-TOP1 F primer | 5'-ACTACCCGGGATGACTATTGCTGATGCTTCC-3' (SEQ ID NO: 40) |
| TOP1-NotI R primer | 5'-TTCAGTGCGGCCGCTTAAAACCTCCAATTTCATCTAC-3' (SEQ ID NO: 41) |
| SmaI-SEN1 F primer | 5'-ACTACCCGGGAAAATGGAATTAGCTAGGATG-3' (SEQ ID NO: 42) |
| SEN1-NotI R primer | 5'-TTCAGTGCGGCCGCAAGATCATGATCTAGGCTTTC-3' (SEQ ID NO: 43) |

Similarly, for yeast cells, 5 μg total RNA was converted into cDNAs by a group of specific primers, including 5' end CAG rt, 3' end CAG rt, and SCR1 rt primers. The amount of cDNAs containing upstream of CAG repeats were measured by the primer set (5' CAG F and 5' CAG R), while the ones with downstream of CAG repeats were detected by 3' CAG F and 3' CAG R primers. SCR1 was included and served as a loading control.

Compounds Treatment of Mouse Striatal Neuronal Cells $Hdh^{Q7/Q7}$ and $Hdh^{Q111/Q111}$ cell lines were first transfected with either control siRNA or siRNA that specifically targets against SUPT4H. After transfection, the cells were incubated with μM tropolone (T89702, Sigma) for 12 hours or 0.3 μM topotecan (T2705, sigma) for 24 hours. Tropolone is a chemical compound that inhibits the enzymatic activity of human RNases H with IC50 of 5.7 μM (Budihas et al, 2005), while topotecan is a nontoxic anticancer drug that inhibits Topoisomerases (Bali et al. 2018).

Western Blotting $Hdh^{Q7/7}$ and $Hdh^{Q111/111}$ cells were lysed in RIPA buffer (50 mM Tris-HCl pH 7.5, 150 mM NaCl, 1% NP-40, 0.1% SDS and 1% sodium deoxycholate) plus 1 mM $Na_3VO_4$, 1 mM DTT, 1 mM PMSF and a protease inhibitor cocktail (Sigma). The supernatants were collected as protein lysats after a high-speed centrifugation.

Equal amounts of protein lysates were heated in sample buffer (60 mM Tris-HCl pH 6.8, 25% glycerol, 4% SDS, 14.4 mM (3-mercaptorthanol, and 0.1% bromophenol blue) and separated on SDS-polyacrylamide gel, followed by transferring to nitrocellulose (NC) membrane. To analyze huntingtin proteins with different length of polyQ, Tris-acetate polyacrylamide gels were used (Liu et al., 2012). Membranes were blocked with TBST (1× TBS, 0.05% tween 20) containing 5% nonfat milk, probed with primary antibodies for 1 hour, washed three times with TBST for 10 minutes, and incubated with secondary antibodies for another 1 hour. After three times TB ST wash, signals were detected using Western Lighting (PerkinElmer Life Sciences).

For Drosophila samples, 15 males and 15 females HD flies were collected after each compound treatment. Their heads were isolated and homogenized with 1× sample buffer (50 mM Tris-HCl pH 7.5, 150 mM NaCl, 1% NP-40, 0.1% sodium dodecyl sulfate (SDS), 1% sodium deoxycholate, and blue dye) for protein lysate collection. Equivalent amounts of protein lysates were separated on 12% SDS-polyacrylamide gel, and then transferred to NC membranes (GE Healthcare Life Science). Detection of HTT and α-tubulin protein was performed as described above.

Fly Stock

The Gmr-gal4-UAS-HTT97Q/cyo line expressing HTT97Q under the control of Gmr-gal4 in compound eyes was provided by MT SU (National Taiwan Normal University, Taipei, Taiwan). Fly stock was maintained and crossed at 25° C. on a standard cornmeal yeast agar medium.

Compounds Treatment of HD Flies

In each compound treatment experiment, 15 Gmr-gal14-UAS-HTT97Q/cyo male flies were crossed with 15 Gmr-gal14-UAS-HTT-97Q/cyo females in a vial containing 10 mL of media supplemented with the testing compound at a final concentration of 10 μM 6CR (Sigma) or/and 100 μM Tropolone (Sigma). 6-chloropurine riboside (6CR) is a chemical reagent that inhibits the activity of SUPT4H by preventing the complex formation of SUPT4H/SUPT5H (Patent No.: US2018/0064744A1). Parent flies were removed after 7 days, and 4-day-old progenies carrying one Gmr-gal14-UAS-HTT97Q allele were collected for eye morphology examination. Digital images of compound eyes were captured by using a camera (CoolSNAP 5.0, Photometrics) mounted onto Leica DMR upright microscope. To increase the depth of field and enhance composite images, software Helicon Focus (HeliconSoft) was applied. In each treatment group, flies were analyzed and normalized with control flies. The control flies were cultured in media containing DMSO (Sigma). Experiments were performed independently three times.

Example 2: Transcription Mediated R-Loop Formation is Affected by the Number of CAG Repeats, but is not Influenced by Spt4 in Yeast Cells Please refer to FIG. 2A-2D. (A) Schematic diagram shown the amplicons by primer set B and primer set Amp on (CAG)n-ADE2 plasmid. (CAG)n-ADE2 possesses either 10, 25, 49, or 99 CAG repeats fused with ADE2 report gene. The fusion genes are under the control of GALL promoter (pGAL1), which can induce (CAG)n-ADE2 expression by growing cells in medium containing 2% galactose. Primer set B amplifies the DNA fragment from the last three CAG repeats to the position 200 bps away from the repeat unit. Primer Amp amplifies amp R gene, which does not generate R-loops, and serves as a control. (B) Analysis of R-loop signal on transcribed (CAG)n-ADE2 by RNA/DNA hybrid precipitation (DIP) method. Wild-type (WT) cells introduced with $(CAG)_{25}$-ADE2, $(CAG)_{49}$-ADE2 or $(CAG)_{99}$-ADE2 were grown in galactose-containing medium and then subjected to DIP analysis. The signal of Amp-RNase H+ samples after input DNA normalization was set as 1. Error bars present mean±SD (N=3; *, P<0.05; , P<0.01; *, P<0.001 by student's t test). (C) Examination of the effect of Spt4 deficiency on the formation of R-loops. Wild-type (WT) and SPT4 gene deletion (ΔS) cells were transformed with $(CAG)_{10}$-ADE2, $(CAG)_{25}$-ADE2 or $(CAG)_{49}$-ADE2 and analyzed as described in (B). (D) Assessment of (CAG)n-ADE2 mRNA expression by Northern blotting in wild-type (WT) and SPT4Δ (ΔS) cells. Cells as described in (C) were collected and subjected to analysis. (CAG)n-ADE2 mRNA was detected by ADE2 probe, and SCR1 served as an internal loading control. After normalization, the level of $(CAG)_{10}$-ADE2 mRNA in WT cells was set as 100%.

The signal of R-loops was diminished by the pre-treatment of samples with RNase H that specifically cleave the RNA moiety of RNA/DNA hybrid (Cerritelli and Crouch, 2009), and thus confirmed the validity of DIP assay for R-loop detection. We found R-loops were detectable in transcribed template with 49 or 99, but not the one with 10 or 25 CAG repeats. In addition, R-loop signal was greater on 99 CAG repeats than on 49 CAG repeats, indicating the probability of R-loops formation is dependent on the number of repeating units. We also found the degree of R-loops in lengthy CAG repeats is not affected by Spt4. However, the transcriptional reduction of CAG-containing genes in Spt4 deficient cells only occurs in the DNA template with R-loop signal.

Example 3: R-Loop Increment Results in a Decreased Production of Transcripts with Lengthy CAG Repeats in Spt4 Deficient Cells Please refer to FIG. 3. (A) Analysis of R-loop signal in wild-type (WT), RNH1Δ (Δ1), SPT4Δ (ΔS) and RNH1Δ SPT4Δ double deletion (Δ1ΔS) cells. These cells were introduced with $(CAG)_{99}$-ADE2, grown in galactose-containing medium, and then collected for R-loop detection by DIP assay. Data presented are normalized with input DNA and compared to Amp-RNase H+ samples as described in FIG. 2(B) (N=3; *, P<0.05; **, P<0.01 by student's t test). (B) Measurement of (CAG)n-ADE2 mRNA expression by Northern blotting in WT, Δ1, ΔS and Δ1ΔS cells. Cells were transformed with $(CAG)_{25}$-ADE2 or $(CAG)_{99}$-ADE2 and then collected for RNA analysis as described in FIG. 2(D). After normalization, the level of $(CAG)_{99}$-ADE2 mRNA in WT cells was set as 100% (N=3) (C) Schematic diagram shown the amplicons by primer sets A and B. Primer set A specifically detects the region, 50 bps upstream of the repetitive sequence to the beginning of first three CAG repeating units. Primer set B amplifies DNA segment downstream of 99 CAG repeats as described in FIG. 2(A). (D) Analysis of transcripts with downstream vs. upstream of CAG repeats by reverse transcription and real-time quantitative PCR. Total RNA was isolated from indicated cells expressing $(CAG)_{99}$-ADE2, and converted into cDNAs by a group of specific reverse transcription (RT) primers. cDNAs were then analyzed by real-time qPCR with primer set A and B as described in (C). Values of B/A ratio are shown in bottom panel.

To evaluate the contribution of R-loops in the transcriptional reduction of genes containing lengthy nucleotide repeats in Spt4 deficient cells, we introduced RNH1 gene deletion in WT and SPT4Δ cells. RNH1 encodes an enzymatic protein that specifically cleaves the RNA moiety of RNA/DNA hybrid (Cerritelli and Crouch, 2009). Thereby, as expected, we found R-loop signal of 99 CAG repeats is substantially increased upon Rnh1 deficiency in the resulting gene deletion stains. With similar extent of R-loop increase in WT and SPT4Δ cells, we found the level of $(CAG)_{99}$-ADE2 mRNA is further decreased in RNH1Δ SPT4Δ cells, compared to it parental SPT4Δ cells. The capacity of transcription machinery to transcribe over the full-length 99 CAG repeats is also declined by increase of R-loops in Spt4 deficient cells. However, transcriptional production of $(CAG)_{99}$-ADE2 is only marginally affected by the change of R-loops in cells with Spt4 proficiency.

Example 4: R-Loop Reduction Results in an Increased Transcript Production of Genes Containing Lengthy Repeats in Spt4 Deficient Cells Please refer to FIG. 4. (A) Schematic diagram illustrating the difference between 99 CAG and 97 CAG/CAA in nucleotide sequence composition. (B) Analysis of R-loop signal in repetitive sequences by DIP assay in WT cells expressing $(CAG)_{99}$-ADE2 and $(CAG/CAA)_{97}$-ADE2. Data are presented as described in FIG. 2(B). (C) Assessment of $(CAG)_{99}$-ADE2 and $(CAG/CAA)_{97}$-ADE2 expression by Northern blotting in wild-type (WT) and SPT4Δ (ΔS) cells. $(CAG)_{99}$-ADE2 and $(CAG/CAA)_{97}$-ADE2 mRNAs were detected by ADE2 probe, and SCR1 served as an internal loading control. After normalization, the level of reporter transcripts in WT cells was set as 100%. (D) Measurement of (CAG)n-ADE2 mRNA abundance by Northern blotting in SPT4Δ cells expressing ectopic SEN1 (D) or TOP1 (E). Sen1/Senataxin and Top1 are negative regulators of R-loops (Kim et al., 1999; Drolet et al, 2006). When cells were cultured in the presence of CuSO4 ($Cu^{2+}$), HA-tagged Sen1 and Top1 were expressed and confirmed by Western blotting (Left panels). (CAG)n-ADE2 mRNA was detected by ADE2 probe, and SCR1 served as an internal loading control. After normalization, the level of $(CAG)_{25}$-ADE2 mRNA in the absence of $Cu^{2+}$ was set as 100% (values are presented as mean±SD).

In order to further evaluate the effect of R-loops on the transcription of genes containing lengthy nucleotide repeats, a DNA template with low degree of R-loops was analyzed in WT and SPT4Δ cells. We found, compared to the one with high level of R-loops, its transcriptional reduction by Spt4 deficiency is diminished. In addition, by ectopic expression of negative regulators of R-loops, we found the transcriptional reduction of genes containing a long stretch of CAG repeats is also diminished in SPT4Δ cells. The collective results, as demonstrated in FIGS. 3 and 4, disclose that R-loops attribute and modulate the transcription elongation impairment of genes containing lengthy repetitive sequences in Spt4 deficient, but not Spt4 proficient cells.

Example 5: R-Loops are Detectable on Transcribed Templates with a Variety of Repetitive Nucleotide Sequences Please refer to FIG. 5. (A) Analysis of R-loop signal by DIP assay in WT cells expressing ADE2 reporter gene with none, 70 CA, 54 CAA, or 41 CAAC repeats. Samples were prepared and analyzed as described in FIG. 2(B). After input DNA normalization, the signal of Amp-RNase H+ samples were set as 1 (N=3, Error bar is presented as mean±SD). (B) Assessment of (CA)n-ADE2 expression by Northern blotting in wild-type (WT) and SPT4Δ cells. $(CA)_n$-ADE2 mRNAs were detected by ADE2 probe, and SCR1 served as an internal loading control. After normalization, the ratio of each $(CA)_n$-ADE2 transcript in SPT4Δ vs. WT cells was quantified and shown in the bottom panel. Likewise, $(CAA)_n$-ADE2, $(CAAC)_n$-ADE2, and $(CAACCA)_n$-ADE2 were analyzed in (C), (D), and (E) respectively.

Here, we found R-loops also occur in transcribed DNA templates with a variety of repetitive nucleotide sequences. Furthermore, the level of transcriptional reduction by Spt4 deficiency is increased upon the increment of number in repeating units.

Figure 6A:
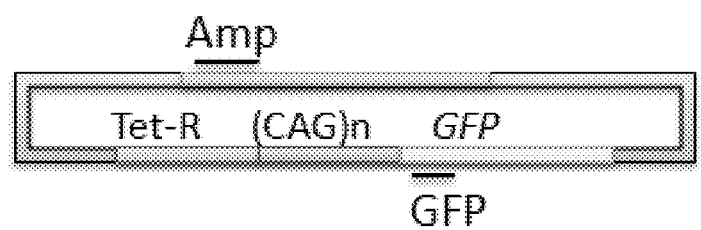
FIG. 6A is a schematic diagram that shows the positions of primer set GFP and Amp on (CAG)n-GFP plasmid.
Figure 6B:
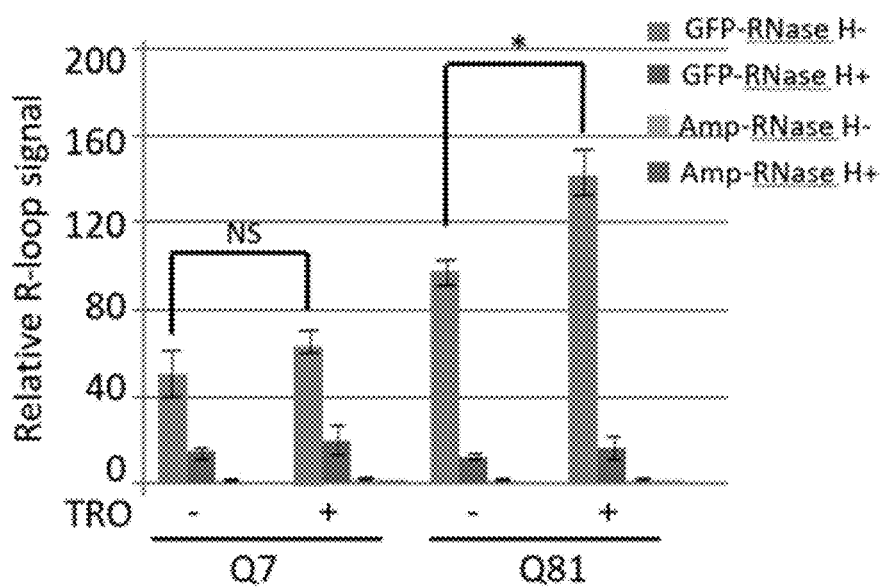
FIG. 6B is a bar graph that shows analysis of R-loops by DIP assay in ST14A cells expressing Q7-GFP or Q81-GFP.
Figure 6C:
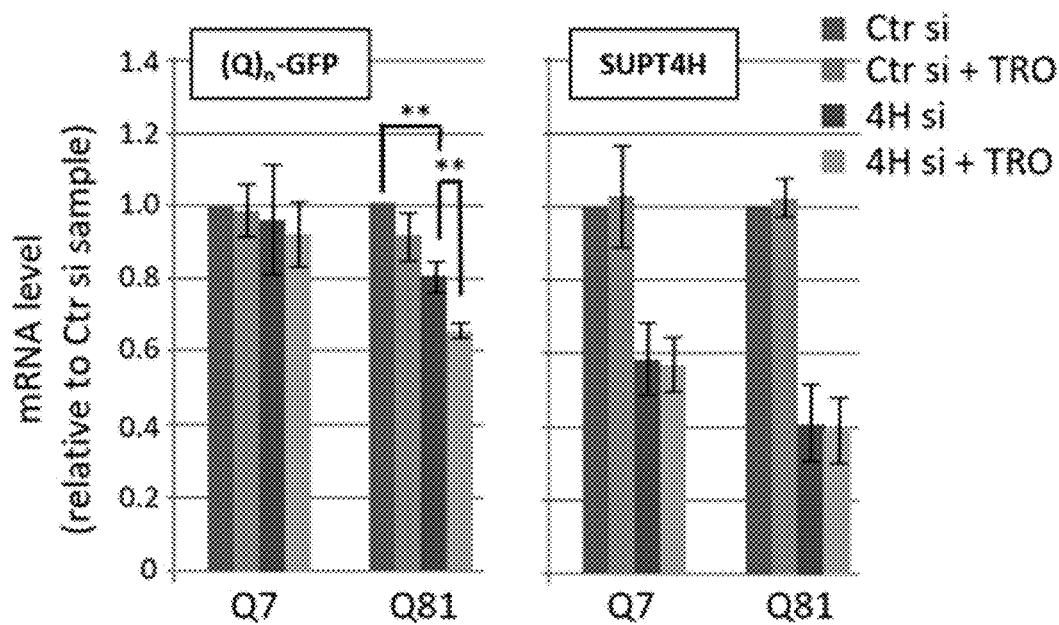
FIG. 6C is a bar graph that shows analysis of (CAG)n-GFP mRNA expression in ST14A cells with SUPT4H siRNA (4H si) knockdown plus tropolone (TRO) treatment.
Figure 6D:
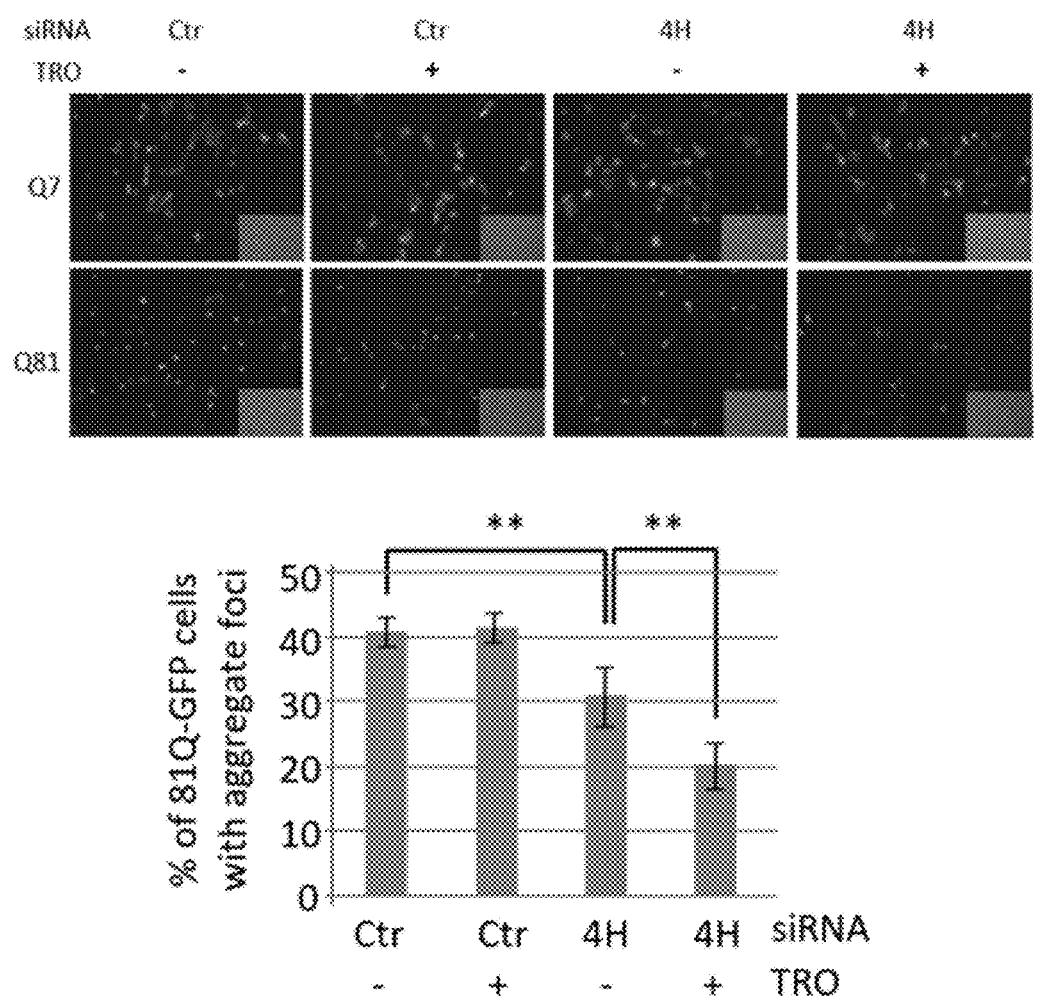
FIG. 6D is a graph that shows analysis of Q81-GFP protein aggregates in ST14A cells with SUPT4H siRNA (4H si) knockdown plus tropolone (TRO) treatment.

Example 6: R-Loop Increment Causes an Increase of Transcriptional Reduction in Genes with Lengthy CAG Repeats in SUPT4H Knockdown Cells Please refer to FIG. 6. (A) Schematic diagram showing the positions of primer set GFP and Amp on (CAG)n-GFP plasmid. (CAG)n-GFP contains either 7 or 81 CAG repeats fused with GFP coding sequence. The fusion gene is under the control of Tet-R promoter. Primer set GFP amplifies the DNA segment in the vicinity of CAG repeats, while primer set Amp amplifies $amp^R$ gene and serves as a control. (B) Analysis of R-loops by DIP assay in ST14A cells expressing Q7-GFP or Q81-GFP. ST14A$^{tet}$ were transfected with pTRE2-(CAG)$_7$-eGFP or pTRE2-(CAG)$_8$i-eGFP, followed by the treatment of tropolone (60 μM) for 12 hours. Tropolone is a chemical reagent that inhibits the enzymatic activity of RNase H (Budihas et al, 2005). As described in FIG. 2(B), the signal of Amp-RNase H+ samples were set as 1 (N=3; NS, no statistical significance; *, P<0.05 by student's t test). A relative high signal of R-loops was detected in (CAG)$_7$-eGFP, but this signal is not increased by tropolone. On the other hand, the high signal of R-loops associated with (CAG)$_8$i-eGFP is significantly increased upon the treatment of tropolone. (C) Analysis of (CAG)n-GFP mRNA expression in ST14A cells with SUPT4H siRNA (4H si) knockdown plus tropolone (TRO) treatment. ST14A$^{tet}$ cells were co-transfected pTRE2-(CAG)n-GFP with SUPT4H siRNA (4H si) or control siRNA (Ctr si), followed by tropolone treatment as described above. RNA was extracted and analyzed by real-time RT-qPCR to measure the quantity of (CAG)n-GFP, SUPT4H and snRNA U6. All samples were normalized with snRNA U6, which is transcribed by RNA polymerase III. The level of RNAs in cells without SUPT4H siRNA knockdown and tropolone treatment was set as 1. (N=3; **, p<0.01 by student's t test). (D) Analysis of Q81-GFP protein aggregates in ST14A cells with SUPT4H siRNA (4H si) knockdown plus tropolone (TRO) treatment. Cells as described in FIG. 6(C) were examined by fluorescent microscopy. Quantification of Q81-GFP cells with aggregation foci is shown at bottom panel.

Figure 7A:
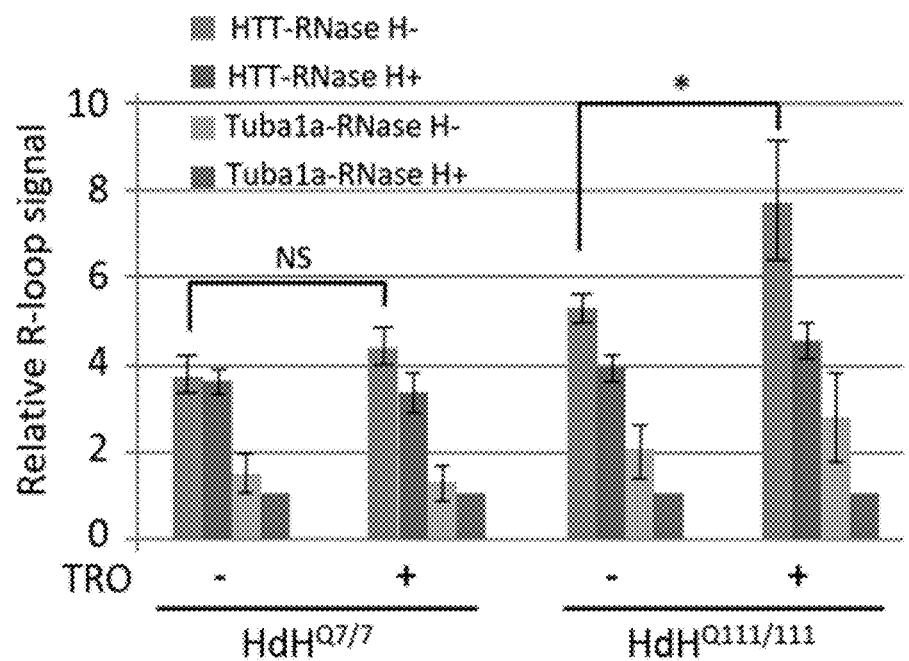
FIG. 7A is a bar graph that shows analysis of R-loops in Hdh$^{Q7/7}$ and Hdh$^{Q111/111}$ cells with tropolone (TRO) treatment.
Figure 7B:
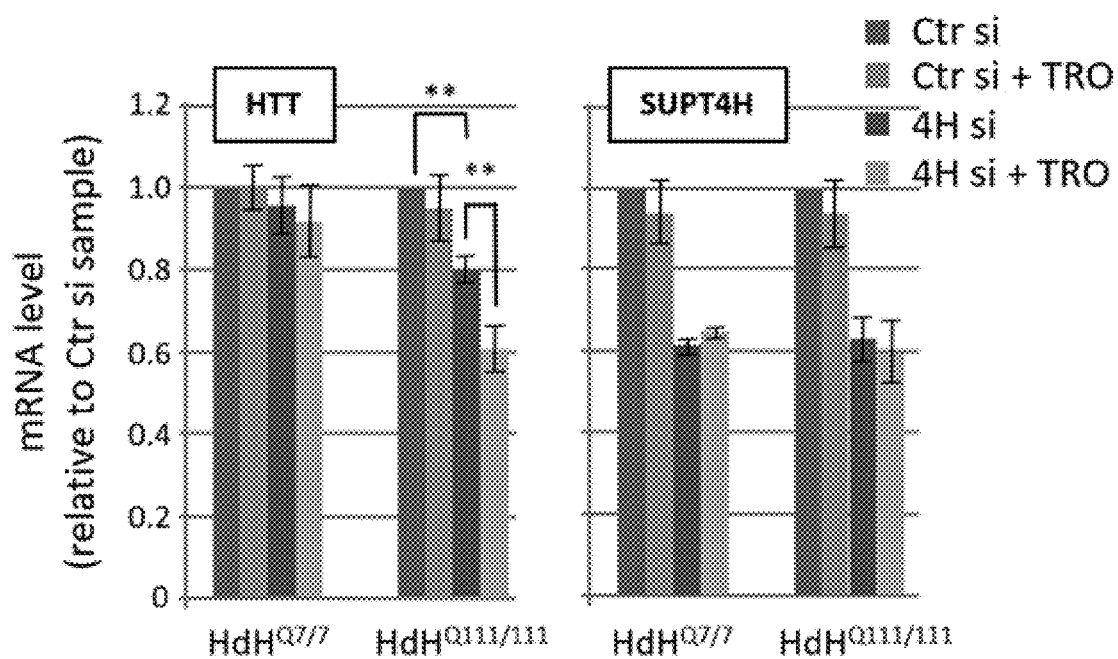
FIG. 7B is a bar graph that shows analysis of HTT mRNA expression in Hdh$^{Q7/7}$ and Hdh$^{Q111/111}$ cells treated with SUPT4H siRNA (4H si) alone or together with tropolone (TRO).
Figure 7C:
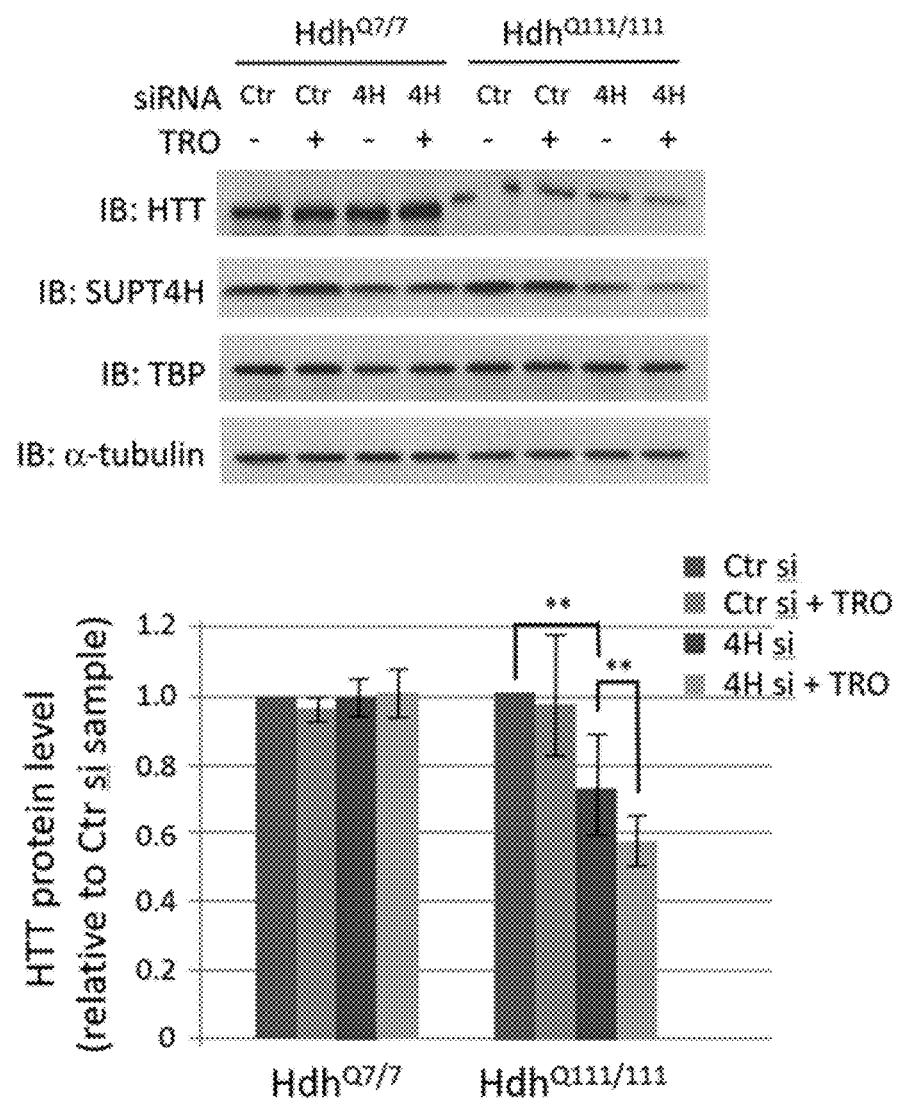
FIG. 7C is a graph that shows analysis of HTT protein expression in Hdh$^{Q7/7}$ and Hdh$^{Q111/111}$ cells treated with SUPT4H siRNA (4H si) alone or together with tropolone (TRO).
Figure 7D:
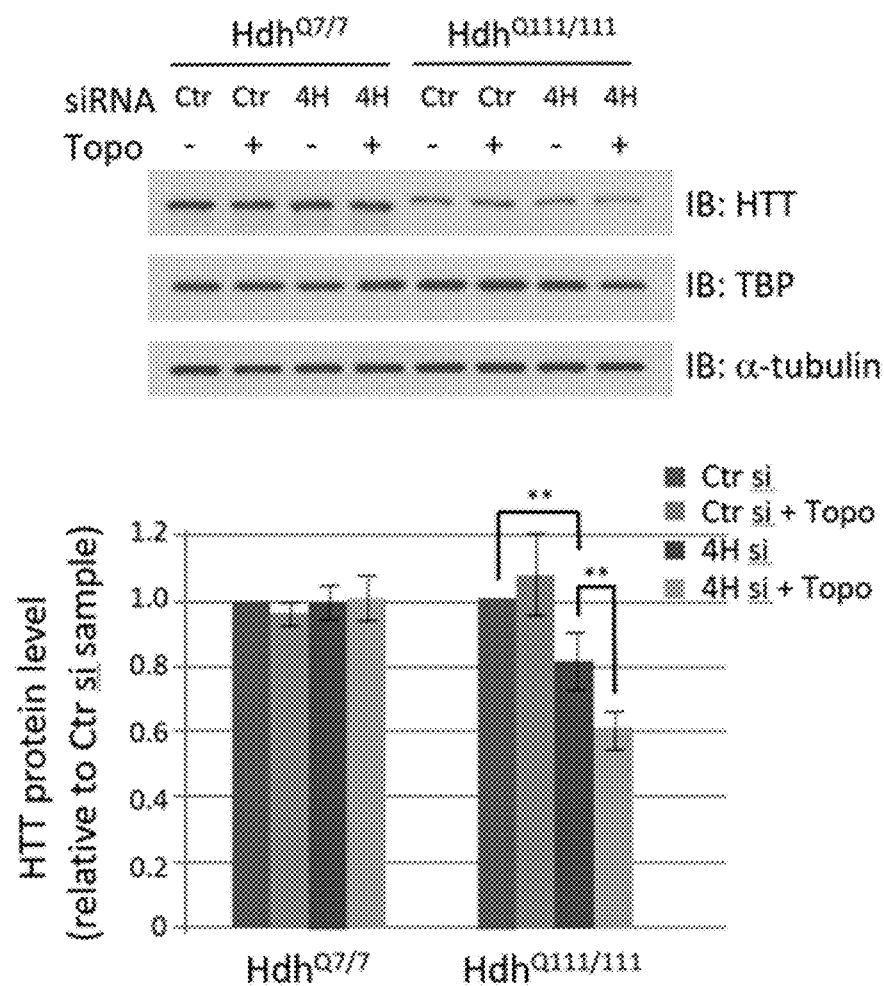
FIG. 7D is a graph that shows analysis of HTT protein expression in Hdh$^{Q7/7}$ and Hdh$^{Q111/111}$ cells treated with SUPT4H siRNA (4H si) alone or together with Topotecan (Topo).

Example 7: The Transcriptional Reduction of Mutant HTT by SUPT4H Knockdown is Further Increased by Pharmacological R-Loop Elevation in Mouse Striatal Neuronal Cells Please refer to FIG. 7. (A) Analysis of R-loops in Hdh$^{Q7/7}$ and Hdh$^{Q111/111}$ cells with tropolone (TRO) treatment. Hdh$^{Q7/7}$ and Hdh$^{Q111/111}$ are mouse striatal neuronal cells that possess homozygous wild-type and mutant huntingtin (HTT) alleles respectively. These cells were incubated with 30 μM tropolone for 12 hours, and then subjected to DIP assay. HTT amplicon was used to probe R-loop signal in the vicinity of CAG repeats in HTT gene and Tubala was included as a control. Similar to FIG. 6(B), the signal of Tubala-RNase H+ samples were set as 1 (N=3; NS, no statistical significance; *, P<0.05 by student's t test). (B) Analysis of HTT mRNA expression in Hdh$^{Q7/7}$ and Hdh$^{Q111/111}$ cells treated with SUPT4H siRNA (4H si) alone or together with tropolone (TRO). The cells were transfected with either SUPT4H siRNA (4H si) or control siRNA (Ctr si), followed by tropolone treatment as described above. RNA was extracted and analyzed by real-time RT-qPCR to measure the quantity of HTT, SUPT4H and snRNA U6. All samples were normalized with snRNA U6, which is transcribed by RNA polymerase III. The level of RNAs in cells without SUPT4H siRNA knockdown and tropolone treatment was set as 1. (N=3; , p<0.01 by student's t test). (C) Analysis of HTT protein expression in Hdh$^{Q7/7}$ and cells treated with SUPT4H siRNA (4H si) alone or together with tropolone (TRO). Cells as described in FIG. 7(B) were collected for Western blot analysis. HTT, SUPT4H, TATA-box binding protein (TBP) were measured. After α-tubulin normalization, the level of HTT in cells without SUPT4H siRNA knockdown and tropolone treatment was set as 1. (N=3; , p<0.01 by student's t test). (D) Analysis of HTT protein expression in Hdh$^{Q7/7}$ and cells treated with SUPT4H siRNA (4H si) alone or together with Topotecan (Topo). Topoisomerases are important cellular enzymes in preventing transcription-coupled R-loops (Drolet, 2006), and topotecan is an anticancer drug that inhibits DNA topoisomerase activity (Bali et al. 2018). Analogous to FIG. 7(C), the quantification of HTT protein levels is shown in bottom panel.

In FIGS. 6 and 7, we demonstrated that chemical reagent tropolone is able to increase R-loops in genes containing lengthy CAG repeats, including mutant HTT, in murine neuronal cells. Upon R-loop increment via the treatment tropolone, we found the level of transcriptional reduction by SUPT4H siRNA knockdown is further increased only in the genes with lengthy repetitive nucleotide sequences. Thereby, it is practical to enhance the transcriptional reduction of mutant genes (with lengthy repetitive nucleotide sequences) in mammalian cells by inhibition of SUPT4H together with the chemical reagents that inhibit the removal of R-loops.

Example 8: Phenotypic Rescue Effect of SUPT4H Inhibitor is Further Improved by Tropolone Co-Treatment in HD-*Drosophila*

Figure 8A:
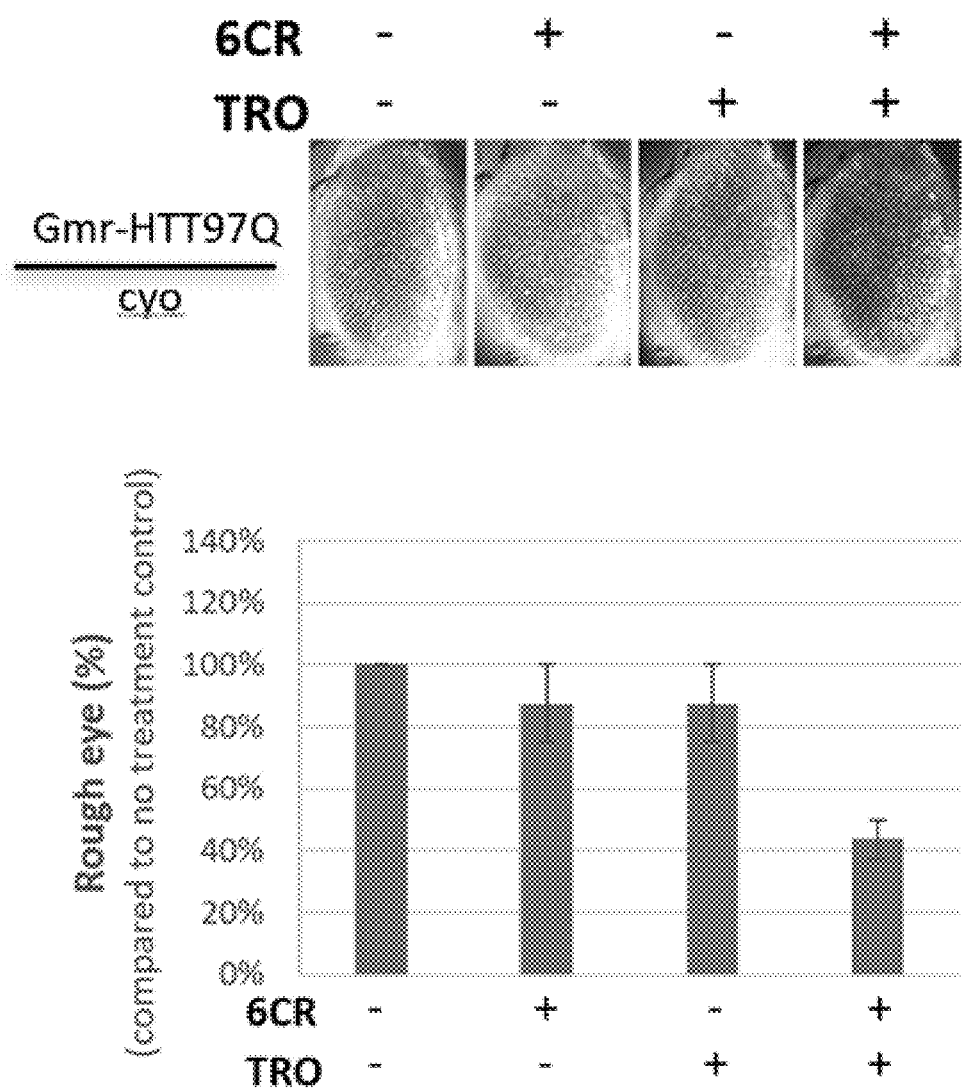
FIG. 8A is a graph that shows analysis of rough eye phenotype, which is caused by the expression of mutant HTT97Q, in HD-*Drosophila*.
Figure 8B:
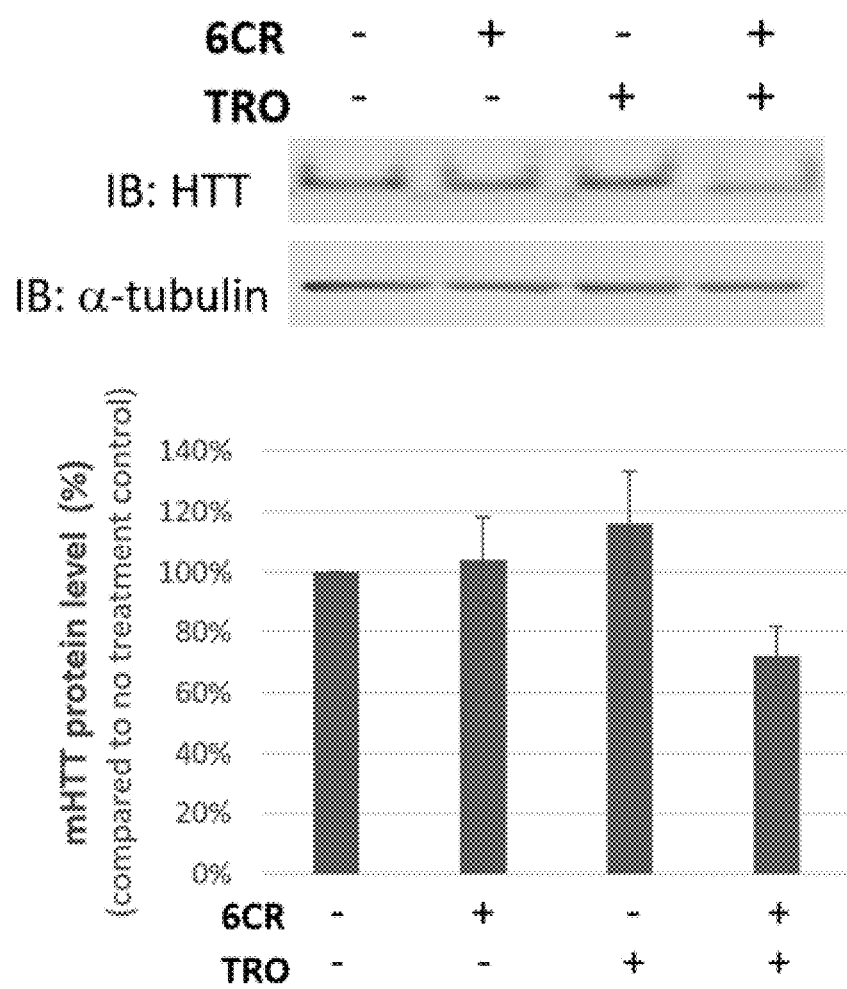
FIG. 8B is a graph that shows analysis of HTT protein expression in HD-*Drosophila*.

Please refer to FIG. 8. (A) Analysis of rough eye phenotype, which is caused by the expression of mutant HTT97Q, in HD-*Drosophila*. 15 Gmr-ga14-UAS-HTT97Q/cyo male flies were crossed with 15 Gmr-ga14-UAS-HTT-97Q/cyo females in a vial containing 10 mL of media supplemented with 6-chloropurine riboside (6CR) and/or Tropolone (TRO). 6-chloropurine riboside (6CR) is a chemical reagent that inhibits the activity of SUPT4H by preventing the complex formation of SUPT4H/SUPT5H (Patent No.: US2018/0064744A1). After parent fly removal, the 4-day-old progenies carrying one Gmr-ga14-UAS-HTT97Q allele were collected and analyzed for eye morphology. 10 flies were examined in each group, and rough eye in control group was set as 100%. The control group was grown in media containing DMSO. (B) Analysis of HTT protein expression in HD-*Drosophila*. 4-day-old progenies as described above were collected and analyzed the levels of mutant HTT by Western blotting. α-tubulin was included and served as a loading control. After normalization, the level of mutant HTT in HD flies without compound treatment was set as 100%.

The *Drosophila melanogaster* (fruit fly) HD model has been well recognized and extensively used as a robust animal model to assess the therapeutic effect of chemical agents on HD manifestations (Marsh et al., 2003). In this study, a transgenic *Drosophila melanogaster* line, Gmr-HTT97Q, which expresses the coding sequence of human HTT exonl with 97 CAG repeats to mimic mutant HTT of HD was employed. The human gene is primarily expressed in the neurons of *Drosophila* compound eyes, resulting in a severe degeneration of photoreceptor neurons and the phenotypic trait 'rough eye'. These phenotypic defects, resulting from degeneration of neurons, are analogous to the loss of neurons by mutant HTT in the brain of HD patients. Here, we found the rescue effect of rough eye phenotype by SUPT4H inhibitor, 6-chloropurine riboside (6CR), is greatly improved with the co-treatment of Tropolone (TRO). In agree with this observation, the level of mutant HTT is decreased accordingly. Thereby, it is practical to enhance the transcriptional reduction of mutant genes (with lengthy repetitive nucleotide sequences) by inhibiting SUPT4H together with the reagents that inhibit the removal of R-loops in animals.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the described embodiments, and without departing from the spirit and scope thereof, can make various changes and modifications of the embodiments to adapt it to various usages and conditions. Thus, other embodiments are also within the claims.

What is claimed is:

1. A method of modulating expression of a gene containing expanded tri-nucleotide repeats in a cell, comprising:
   administering to the cell a composition comprising an oligonucleotide that is complementary to a nucleic acid encoding SPT4 or SUPT4H, wherein the oligonucleotide is a siRNA, a shRNA, an antisense oligonucleotide, or a chemical reagent that is 6-chloropurine riboside; and
   administering a compound that enhances R-loop formation, wherein the compound is selected from a topoisomerase inhibitor or an RNase H inhibitor,
   wherein the gene contains a segment of DNA with CAG or CTG tri-nucleotide repeats that are prone to R-loop formation.

2. The method of claim 1, wherein the oligonucleotide is SUPT4H siRNA.

3. The method of claim 1, wherein the topoisomerase inhibitor is topotecan.

4. The method of claim 1, wherein the RNase H inhibitor is tropolone.

5. A method of inhibiting transcription of a gene containing expanded tri-nucleotide repeats in a cell, comprising:
   administering to the cell a compound selected from an oligonucleotide that is complementary to a nucleic acid encoding SPT4 or SUPT4H, wherein the oligonucleotide is a siRNA, a shRNA, an antisense oligonucleotide, or a chemical reagent 6-chloropurine riboside; and
   administering a compound that enhances R-loop formation, wherein the compound that enhances R-loop formation is selected from a topoisomerase inhibitor or an RNase H inhibitor,
   wherein the gene contains a segment of DNA with CAG or CTG tri-nucleotide repeats that are prone to R-loop formation.

6. The method of claim 5, wherein the oligonucleotide is SUPT4H siRNA.

7. The method of claim 5, wherein the RNase H inhibitor is tropolone.

8. The method of claim 5, wherein the topoisomerase inhibitor is topotecan.

9. A method of enhancing drug therapy of a tri-nucleotide repeat expansion disease in a subject in need thereof, comprising administering to said subject an R-loop regulating compound with a tri-nucleotide repeat expansion drug, wherein the tri-nucleotide repeat expansion drug is an oligonucleotide that is complementary to a nucleic acid encoding SPT4 or SUPT4H, wherein the oligonucleotide is a siRNA, a shRNA, an antisense oligonucleotide, or the drug is 6-chloropurine riboside, wherein the R-loop regulating compound is selected from a topoisomerase inhibitor or an RNase H inhibitor, wherein the gene contains a segment of DNA with CAG or CTG tri-nucleotide repeats that are prone to R-loop formation.

10. The method of claim 9, wherein the tri-nucleotide repeat expansion disease is selected from the group consisting of spinocerebellar ataxia type 1, 2, 3, 7, 17, dentatorubral-pallidoluysian atrophy, spinal bulbar muscular atrophy, myotonic atrophy type 1 and Huntington's disease.

11. The method of claim 9, wherein the oligonucleotide is SUPT4H siRNA, the RNase H inhibitor is tropolone.

12. The method of claim 9, wherein the topoisomerase inhibitor is topotecan.

* * * * *

SEQUENCE LISTING

```
<160> NUMBER OF SEQ ID NOS: 45

<210> SEQ ID NO 1
<211> LENGTH: 21
<212> TYPE: RNA
<213> ORGANISM: Artificial Sequence
<220> FEATURE:
<223> OTHER INFORMATION: is used to knock-down SUPT4H expression in mice

<400> SEQUENCE: 1
uggccuacaa aucgagagau u                                             21

<210> SEQ ID NO 2
<211> LENGTH: 21
<212> TYPE: RNA
<213> ORGANISM: Artificial Sequence
<220> FEATURE:
<223> OTHER INFORMATION: is used to knock-down SUPT4H expression in rat
      cells

<400> SEQUENCE: 2
ucucucgauu uguaggccau u                                             21

<210> SEQ ID NO 3
<211> LENGTH: 22
<212> TYPE: DNA
<213> ORGANISM: Artificial Sequence
<220> FEATURE:
<223> OTHER INFORMATION: ADE2-F primer. The primer sequence synthesized
      from the laboratory.

<400> SEQUENCE: 3
tccggaagct ttggaagtac tg                                            22

<210> SEQ ID NO 4
<211> LENGTH: 22
<212> TYPE: DNA
<213> ORGANISM: Artificial Sequence
<220> FEATURE:
<223> OTHER INFORMATION: ADE2-R primer. The primer sequence synthesized
      from the laboratory.

<400> SEQUENCE: 4
taagttgaac ggagtccgga ac                                            22
```

<210> SEQ ID NO 5
<211> LENGTH: 21
<212> TYPE: DNA
<213> ORGANISM: Artificial Sequence
<220> FEATURE:
<223> OTHER INFORMATION: SCR1-F primer. The primer sequence synthesized
      from the laboratory.

<400> SEQUENCE: 5
ggctgtaatg gctttctggt g                                             21

<210> SEQ ID NO 6
<211> LENGTH: 21
<212> TYPE: DNA
<213> ORGANISM: Artificial Sequence
<220> FEATURE:
<223> OTHER INFORMATION: SCR1-R primer. The primer sequence synthesized
      from the laboratory.

<400> SEQUENCE: 6
accagacaga gagacggatt c                                             21

<210> SEQ ID NO 7
<211> LENGTH: 23
<212> TYPE: DNA
<213> ORGANISM: Artificial Sequence
<220> FEATURE:
<223> OTHER INFORMATION: Primer-B F primer. The primer sequence
      synthesized from the laboratory.

<400> SEQUENCE: 7
cagcagcagg ggggatccga ttc                                           23

<210> SEQ ID NO 8
<211> LENGTH: 29
<212> TYPE: DNA
<213> ORGANISM: Artificial Sequence
<220> FEATURE:
<223> OTHER INFORMATION: Primer-B' F primer. The primer sequence
      synthesized from the laboratory.

<400> SEQUENCE: 8
cgggatccat ggattctaga acagttggt                                     29

<210> SEQ ID NO 9
<211> LENGTH: 26
<212> TYPE: DNA
<213> ORGANISM: Artificial Sequence
<220> FEATURE:
<223> OTHER INFORMATION: Primer-B R primer. The primer sequence
      synthesized from the laboratory.

<400> SEQUENCE: 9
tcagctagtt tttcgatatc aagagg                                        26

<210> SEQ ID NO 10
<211> LENGTH: 21
<212> TYPE: DNA
<213> ORGANISM: Artificial Sequence
<220> FEATURE:
<223> OTHER INFORMATION: AMP F primer. The primer sequence synthesized
      from the laboratory.

<400> SEQUENCE: 10
ttaatcagtg aggcacctat c                                             21

<210> SEQ ID NO 11
<211> LENGTH: 21
<212> TYPE: DNA
<213> ORGANISM: Artificial Sequence
<220> FEATURE:
<223> OTHER INFORMATION: AMP R primer. The primer sequence synthesized
      from the laboratory.

<400> SEQUENCE: 11
atcatgtaac tcgccttgat c                                             21

<210> SEQ ID NO 12
<211> LENGTH: 24
<212> TYPE: DNA
<213> ORGANISM: Artificial Sequence
<220> FEATURE:
<223> OTHER INFORMATION: ST14A eGFP F primer. The primer sequence
      synthesized from the laboratory.

<400> SEQUENCE: 12
ctgaacttgt ggccgtttac gtcg                                          24

<210> SEQ ID NO 13
<211> LENGTH: 29
<212> TYPE: DNA
<213> ORGANISM: Artificial Sequence
<220> FEATURE:
<223> OTHER INFORMATION: ST14A eGFP R primer. The primer sequence
      synthesized from the laboratory.

<400> SEQUENCE: 13
tcccccgggg atggtgagca agggcgagg                                     29

<210> SEQ ID NO 14
<211> LENGTH: 21
<212> TYPE: DNA
<213> ORGANISM: Artificial Sequence
<220> FEATURE:
<223> OTHER INFORMATION: AMP F primer. The primer sequence synthesized
      from the laboratory.

<400> SEQUENCE: 14
ttaatcagtg aggcacctat c                                             21

<210> SEQ ID NO 15
<211> LENGTH: 21
<212> TYPE: DNA
<213> ORGANISM: Artificial Sequence
<220> FEATURE:
<223> OTHER INFORMATION: AMP R primer. The primer sequence synthesized
      from the laboratory.

<400> SEQUENCE: 15
atcatgtaac tcgccttgat c                                             21

<210> SEQ ID NO 16
<211> LENGTH: 20
<212> TYPE: DNA
<213> ORGANISM: Artificial Sequence
<220> FEATURE:
<223> OTHER INFORMATION: Mouse HTT DIP F primer. The primer sequence
      synthesized from the laboratory.

<400> SEQUENCE: 16
cgcctcctca gcttcctcag                                               20

```
<210> SEQ ID NO 17
<211> LENGTH: 20
<212> TYPE: DNA
<213> ORGANISM: Artificial Sequence
<220> FEATURE:
<223> OTHER INFORMATION: Mouse HTT DIP R primer. The primer sequence
      synthesized from the laboratory.

<400> SEQUENCE: 17
ggttgctggg tcactctgtc                                               20

<210> SEQ ID NO 18
<211> LENGTH: 21
<212> TYPE: DNA
<213> ORGANISM: Artificial Sequence
<220> FEATURE:
<223> OTHER INFORMATION: Mouse Tuba1a DIP F primer. The primer sequence
      synthesized from the laboratory.

<400> SEQUENCE: 18
ccattggcaa ggagatcatt g                                             21

<210> SEQ ID NO 19
<211> LENGTH: 21
<212> TYPE: DNA
<213> ORGANISM: Artificial Sequence
<220> FEATURE:
<223> OTHER INFORMATION: Mouse Tuba1a DIP R primer. The primer sequence
      synthesized from the laboratory.

<400> SEQUENCE: 19
atggcctcat tgtctaccat g                                             21

<210> SEQ ID NO 20
<211> LENGTH: 21
<212> TYPE: DNA
<213> ORGANISM: Artificial Sequence
<220> FEATURE:
<223> OTHER INFORMATION: 5' end CAG rt primer. The primer sequence
      synthesized from the laboratory.

<400> SEQUENCE: 20
ctgctgctgc tgctgctgct g                                             21

<210> SEQ ID NO 21
<211> LENGTH: 22
<212> TYPE: DNA
<213> ORGANISM: Artificial Sequence
<220> FEATURE:
<223> OTHER INFORMATION: 3' end CAG rt primer. The primer sequence
      synthesized from the laboratory.

<400> SEQUENCE: 21
taagttgaac ggagtccgga ac                                            22

<210> SEQ ID NO 22
<211> LENGTH: 21
<212> TYPE: DNA
<213> ORGANISM: Artificial Sequence
<220> FEATURE:
<223> OTHER INFORMATION: SCR1 rt primer. The primer sequence
      synthesized from the laboratory.

<400> SEQUENCE: 22
accagacaga gagacggatt c                                             21

<210> SEQ ID NO 23
```

-continued

```
<211> LENGTH: 20
<212> TYPE: DNA
<213> ORGANISM: Artificial Sequence
<220> FEATURE:
<223> OTHER INFORMATION: 5' CAG F primer. The primer sequence
      synthesized from the laboratory.

<400> SEQUENCE: 23
actacaagga cgacgatgac                                                   20

<210> SEQ ID NO 24
<211> LENGTH: 20
<212> TYPE: DNA
<213> ORGANISM: Artificial Sequence
<220> FEATURE:
<223> OTHER INFORMATION: 5' CAG R primer. The primer sequence
      synthesized from the laboratory.

<400> SEQUENCE: 24
ctgctgctgg ggtttgaggg                                                   20

<210> SEQ ID NO 25
<211> LENGTH: 23
<212> TYPE: DNA
<213> ORGANISM: Artificial Sequence
<220> FEATURE:
<223> OTHER INFORMATION: 3' CAG F primer. The primer sequence
      synthesized from the laboratory.

<400> SEQUENCE: 25
cagcagcagg ggggatccga ttc                                               23

<210> SEQ ID NO 26
<211> LENGTH: 26
<212> TYPE: DNA
<213> ORGANISM: Artificial Sequence
<220> FEATURE:
<223> OTHER INFORMATION: 3' CAG R primer. The primer sequence
      synthesized from the laboratory.

<400> SEQUENCE: 26
tcagctagtt tttcgatatc aagagg                                            26

<210> SEQ ID NO 27
<211> LENGTH: 21
<212> TYPE: DNA
<213> ORGANISM: Artificial Sequence
<220> FEATURE:
<223> OTHER INFORMATION: SCR1 F primer. The primer sequence synthesized
      from the laboratory.

<400> SEQUENCE: 27
ggctgtaatg gctttctggt g                                                 21

<210> SEQ ID NO 28
<211> LENGTH: 21
<212> TYPE: DNA
<213> ORGANISM: Artificial Sequence
<220> FEATURE:
<223> OTHER INFORMATION: SCR1 R primer. The primer sequence synthesized
      from the laboratory.

<400> SEQUENCE: 28
accagacaga gagacggatt c                                                 21

<210> SEQ ID NO 29
<211> LENGTH: 22
```

```
<212> TYPE: DNA
<213> ORGANISM: Artificial Sequence
<220> FEATURE:
<223> OTHER INFORMATION: snRNA U6 rt primer. The primer sequence
      synthesized from the laboratory.

<400> SEQUENCE: 29
aaaaatatgg aacgcttcac ga                                            22

<210> SEQ ID NO 30
<211> LENGTH: 20
<212> TYPE: DNA
<213> ORGANISM: Artificial Sequence
<220> FEATURE:
<223> OTHER INFORMATION: snRNA U6 F primer. The primer sequence
      synthesized from the laboratory.

<400> SEQUENCE: 30
ctcgcttcgg cagcacatat                                               20

<210> SEQ ID NO 31
<211> LENGTH: 22
<212> TYPE: DNA
<213> ORGANISM: Artificial Sequence
<220> FEATURE:
<223> OTHER INFORMATION: snRNA U6 R primer. The primer sequence
      synthesized from the laboratory.

<400> SEQUENCE: 31
tatggaacgc ttcacgaatt tg                                            22

<210> SEQ ID NO 32
<211> LENGTH: 20
<212> TYPE: DNA
<213> ORGANISM: Artificial Sequence
<220> FEATURE:
<223> OTHER INFORMATION: rat SUPT4H F primer. The primer sequence
      synthesized from the laboratory.

<400> SEQUENCE: 32
cctggtgtac cctcctttga                                               20

<210> SEQ ID NO 33
<211> LENGTH: 20
<212> TYPE: DNA
<213> ORGANISM: Artificial Sequence
<220> FEATURE:
<223> OTHER INFORMATION: rat SUPT4H R primer. The primer sequence
      synthesized from the laboratory.

<400> SEQUENCE: 33
attacccatg gctcccttct                                               20

<210> SEQ ID NO 34
<211> LENGTH: 24
<212> TYPE: DNA
<213> ORGANISM: Artificial Sequence
<220> FEATURE:
<223> OTHER INFORMATION: eGFP F primer. The primer sequence synthesized
      from the laboratory.

<400> SEQUENCE: 34
ctgaacttgt ggccgtttac gtcg                                          24

<210> SEQ ID NO 35
<211> LENGTH: 29
<212> TYPE: DNA
```

<213> ORGANISM: Artificial Sequence
<220> FEATURE:
<223> OTHER INFORMATION: eGFP R primer. The primer sequence synthesized from the laboratory.

<400> SEQUENCE: 35
tcccccgggg atggtgagca agggcgagg                29

<210> SEQ ID NO 36
<211> LENGTH: 21
<212> TYPE: DNA
<213> ORGANISM: Artificial Sequence
<220> FEATURE:
<223> OTHER INFORMATION: Mouse SUPT4H F primer. The primer sequence synthesized from the laboratory.

<400> SEQUENCE: 36
tcattgcgat gatgagtcca g                21

<210> SEQ ID NO 37
<211> LENGTH: 21
<212> TYPE: DNA
<213> ORGANISM: Artificial Sequence
<220> FEATURE:
<223> OTHER INFORMATION: Mouse SUPT4H R primer. The primer sequence synthesized from the laboratory.

<400> SEQUENCE: 37
tttcgtggag tctgctgatt c                21

<210> SEQ ID NO 38
<211> LENGTH: 21
<212> TYPE: DNA
<213> ORGANISM: Artificial Sequence
<220> FEATURE:
<223> OTHER INFORMATION: Mouse HTT F primer. The primer sequence synthesized from the laboratory.

<400> SEQUENCE: 38
tcctgatcag tgaagtggtt c                21

<210> SEQ ID NO 39
<211> LENGTH: 21
<212> TYPE: DNA
<213> ORGANISM: Artificial Sequence
<220> FEATURE:
<223> OTHER INFORMATION: Mouse HTT R primer. The primer sequence synthesized from the laboratory.

<400> SEQUENCE: 39
gtcacactcc aacacataga g                21

<210> SEQ ID NO 40
<211> LENGTH: 31
<212> TYPE: DNA
<213> ORGANISM: Artificial Sequence
<220> FEATURE:
<223> OTHER INFORMATION: SmaI- TOP1 F primer. The primer sequence synthesized from the laboratory.

<400> SEQUENCE: 40
actacccggg atgactattg ctgatgcttc c                31

<210> SEQ ID NO 41
<211> LENGTH: 37
<212> TYPE: DNA
<213> ORGANISM: Artificial Sequence

```
<220> FEATURE:
<223> OTHER INFORMATION: TOP1-NotI R primer. The primer sequence
      synthesized from the laboratory.

<400> SEQUENCE: 41
ttcagtgcgg ccgcttaaaa cctccaattt catctac                                37

<210> SEQ ID NO 42
<211> LENGTH: 31
<212> TYPE: DNA
<213> ORGANISM: Artificial Sequence
<220> FEATURE:
<223> OTHER INFORMATION: SmaI-SEN1 F primer. The primer sequence
      synthesized from the laboratory.

<400> SEQUENCE: 42
actacccggg aaaatggaat tagctaggat g                                      31

<210> SEQ ID NO 43
<211> LENGTH: 35
<212> TYPE: DNA
<213> ORGANISM: Artificial Sequence
<220> FEATURE:
<223> OTHER INFORMATION: SEN1-NotI R primer. The primer sequence
      synthesized from the laboratory.

<400> SEQUENCE: 43
ttcagtgcgg ccgcaagatc atgatctagg ctttc                                  35

<210> SEQ ID NO 44
<211> LENGTH: 297
<212> TYPE: DNA
<213> ORGANISM: Artificial Sequence
<220> FEATURE:
<223> OTHER INFORMATION: 99 CAG in nucleotide sequence composition

<400> SEQUENCE: 44
cagcagcagc agcagcagca gcagcagcag cagcagcagc agcagcagca gcagcagcag        60
cagcagcagc agcagcagca gcagcagcag cagcagcagc agcagcagca gcagcagcag       120
cagcagcagc agcagcagca gcagcagcag cagcagcagc agcagcagca gcagcagcag       180
cagcagcagc agcagcagca gcagcagcag cagcagcagc agcagcagca gcagcagcag       240
cagcagcagc agcagcagca gcagcagcag cagcagcagc agcagcagca gcagcag          297

<210> SEQ ID NO 45
<211> LENGTH: 291
<212> TYPE: DNA
<213> ORGANISM: Artificial Sequence
<220> FEATURE:
<223> OTHER INFORMATION: 97 CAG/CAA in nucleotide sequence composition

<400> SEQUENCE: 45
cagcagcagc aacagcaaca acagcagcaa cagcaacaac agcagcaaca gcaacaacag        60
cagcaacagc aacaacagca gcaacagcaa caacagcagc aacagcaaca acagcagcaa       120
cagcaacaac agcagcaaca gcaacaacag cagcaacagc aacaacagca gcaacagcaa       180
caacagcagc aacagcaaca acagcagcaa cagcaacaac agcagcaaca gcaacaacag       240
cagcaacagc aacaacagca gcaacagcaa caacagcagc aacagcaaca a                291
```